US008449886B2

(12) United States Patent
Jure-Kunkel

(10) Patent No.: US 8,449,886 B2
(45) Date of Patent: May 28, 2013

(54) COMBINATION OF ANTI-CTLA4 ANTIBODY WITH TUBULIN MODULATING AGENTS FOR THE TREATMENT OF PROLIFERATIVE DISEASES

(75) Inventor: Maria Jure-Kunkel, Plainsboro, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 206 days.

(21) Appl. No.: 12/811,867

(22) PCT Filed: Jan. 7, 2009

(86) PCT No.: PCT/US2009/030291
§ 371 (c)(1),
(2), (4) Date: Jul. 7, 2010

(87) PCT Pub. No.: WO2009/089260
PCT Pub. Date: Jul. 16, 2009

(65) Prior Publication Data
US 2010/0278828 A1    Nov. 4, 2010

Related U.S. Application Data

(60) Provisional application No. 61/019,778, filed on Jan. 8, 2008, provisional application No. 61/056,957, filed on May 29, 2008.

(51) Int. Cl.
*A61K 39/00* (2006.01)
*A61K 39/395* (2006.01)
*A61K 31/425* (2006.01)

(52) U.S. Cl.
USPC .................. 424/142.1; 424/174.1; 514/365

(58) Field of Classification Search
USPC .................. 424/142.1, 174.1; 514/365
See application file for complete search history.

(56) References Cited

U.S. PATENT DOCUMENTS

| 6,605,599 | B1 | 8/2003 | Vite et al. |
| 6,984,720 | B1 | 1/2006 | Korman et al. |
| 7,008,936 | B2 | 3/2006 | Voi et al. |
| 7,312,237 | B2 | 12/2007 | Lee |
| 2005/0123536 | A1 | 6/2005 | Law et al. |

FOREIGN PATENT DOCUMENTS

| EP | 1262193 A1 | 12/2002 |
| WO | WO9902514 | 1/1999 |
| WO | WO0114424 A2 | 3/2001 |
| WO | WO2006048749 A1 | 5/2006 |
| WO | WO2006101691 A1 | 9/2006 |
| WO | WO2006105399 A1 | 10/2006 |
| WO | WO2007113648 A2 | 10/2007 |

OTHER PUBLICATIONS

Beck KE, Blansfield JA, Tran KQ, Feldman AL, Hughes MS, Royal RE, Kammula US, Topalian SL, Sherry RM, Kleiner D, Quezado M, Lowy I, Yellin M, Rosenberg SA, Yang JC. Enterocolitis in patients with cancer after antibody blockade of cytotoxic T-lymphocyte-associated antigen 4. J Clin Oncol. May 20, 2006;24(15):2283-9.*
Leach DR, Krummel MF, Allison JP. Enhancement of antitumor immunity by CTLA-4 blockade. Science. Mar. 22, 1996;271(5256):1734-6.*
Lee FY, Borzilleri R, Fairchild CR, Kim SH, Long BH, Reventos-Suarez C, Vite GD, Rose WC, Kramer RA. BMS-247550: a novel epothilone analog with a mode of action similar to paclitaxel but possessing superior antitumor efficacy. Clin Cancer Res. May 2001;7(5):1429-37.*
Mani S, McDaid H, Hamilton A, Hochster H, Cohen MB, Khabelle D, Griffin T, Lebwohl DE, Liebes L, Muggia F, Horwitz SB. Phase I clinical and pharmacokinetic study of BMS-247550, a novel derivative of epothilone B, in solid tumors. Clin Cancer Res. Feb. 15, 2004;10(4):1289-98.*
Weber J. Review: anti-CTLA-4 antibody ipilimumab: case studies of clinical response and immune-related adverse events. Oncologist. Jul. 2007;12(7):864-72.*
Alegre, et al., "T-Cell Regulation by CD28 and CTLA-4", Nature Reviews/Immunology, vol. 1, pp. 220-228 (2001).
Bretscher, et al., "A Theory of Self-Nonself Discrimination", Science, vol. 169, pp. 1042-1049 (1970).
Brunet, et al., "A new member of the immunoglobulin superfamily—CTLA-4", Nature, vol. 328, pp. 267-270 (1987).
Brunner, et al., "CTLA-4-Mediated Inhibition of Early Events of T Cell Proliferation", J. Immunol, vol. 162, pp. 5813-5820 (1999).
Gehan, Edmund A., "A generalized Wilcoxon test for comparing arbitrarily singly-censored samples", Biometrika, vol. 52 (1,2), pp. 203-223 (1965).
Giannakakou, et al., "Paclitaxel-resistant Human Ovarian Cancer Cells Have Mutant β-Tubulins that Exhibit Impaired Paclitaxel-driven Polymerization", J. Biol. Chem., vol. 272 (27), pp. 17118-17125 (1997).
Greenwald, et al., "CTLA-4 regulates cell cycle progression during a primary immune response", Eur. J. Immunol., vol. 32, pp. 366-373 (2002).
Gross, et al., "Identification and Distribution of the Costimulatory Receptor CD28 in the Mouse", J. Immunol., vol. 149, pp. 380-388 (1992).
Höfle, et al., Chapter 21: "Epothilone, a Myxobacterial Metabolite with Promising Antitumor Activity", Anticancer Agents from Natural Products, pp. 213-250, CRC Press, publ., Cragg, G.M. et al., eds. (2005).
Hurwitz, et al., "Combination Immunotherapy of Primary Prostate Cancer in a Transgenic Mouse Model Using CTLA-4 Blockade", Cancer Res., vol. 60, pp. 2444-2448 (2000).
Jure-Kunkel, et al., "Antitumor activity of anti-CTLA-4 monoclonal antibody (mAb) in combination with ixabepilone in preclinical tumor models", J. Clin. Oncol., vol. 26, No. 155 (May 20 Supplement) 2008:3048 Abstract.
Krummel, et al., "CTLA-4 Engagement Inhibits IL-2 Accumulation and Cell Cycle Progression upon Activation of Resting T Cells", J. Exp. Med., vol. 183, pp. 2533-2540 (1996).
Leach, et al., "Enhancement of Antitumor Immunity by CTLA-4 Blockade", Science, vol. 271, pp. 1734-1736 (1996).
Lee, et al., "BMS-247550: A Novel Epothilone Analog with a Mode of Action Similar to Paclitaxel but Possessing Superior Antitumor Efficacy", Clin. Canc. Res., vol. 7, pp. 1429-1437 (2001).
Lindsten, et al., "Characterization of CTLA-4 Structure and Expression on Human T Cells", J. Immunol., vol. 151 (7), pp. 3489-3499 (1993).
Linsley, et al., "Binding of the B Cell Activation Antigen B7 to CD28 Costimulates T Cell Proliferation and Interleukin 2 mRNA Accumulation", J. Exp. Med., vol. 173, pp. 721-730 (1991).

(Continued)

*Primary Examiner* — Paul Zarek
(74) *Attorney, Agent, or Firm* — Stephen C. D'Amico

(57) ABSTRACT

Compositions and methods are disclosed which are useful for the treatment and prevention of proliferative disorders, and which comprise an anti-CTLA4 antagonist with a tubulin modulating agent.

5 Claims, 4 Drawing Sheets

OTHER PUBLICATIONS

Linsley, et al., "Human B7-1 (CD80) and B7-2 (CD86) Bind with Similar Avidities but Distinct Kinetics to CD28 and CTLA-4 Receptors", Immunity, vol. 1, pp. 793-801 (1994).

Long, et al., "Mechanisms of Resistance to Etoposide and Teniposide in Acquired Resistant Human Colon and Lung Carcinoma Cell Lines", Cancer Res., vol. 51, pp. 5275-5284 (1991).

Long, et al., "Paclitaxel Inhibits Progression of Mitotic Cells to $G_1$ Phase by Interference with Spindle Formation without Affecting Other Microtubule Functions during Anaphase and Telephase", Cancer Res., vol. 54, pp. 4355-4361 (1994).

Riss, et al., Comparison of MTT, XTT, and a novel tetrazolium compound MTS for in vitro proliferation and chemosensitivity assays, Mol Biol. Cell, 3 (Suppl.): 184a (1992).

Schwartz, Ronald H., "A Cell Culture Model for T Lymphocyte Clonal Anergy", Science, vol. 248, pp. 1349-1356 (1990).

Van Elsas, et al., "Elucidating the Autoimmune and Antitumor Effector Mechanisms of a Treatment Based on Cytotoxic T Lymphocyte Antigen-4 Blockade in Combination with a B16 Melanoma Vaccine: Comparison of Prophylaxis and Therapy", J. Exp. Med., vol. 194 (4), pp. 481-489 (2001).

Van Elsas, et al., "Combination Immunotherapy of B16 Melanoma Using Anti-Cytotoxic T Lymphocyte-associated Antigen 4 (CTLA-4) and Granulocyte/Macrophage Colony-Stimulating Factor (GM-CSF)-producing Vaccines Induces Rejection of Subcutaneous and Metastatic Tumors Accompanied by Autoimmune Depigmentation", J. Exp. Med., vol. 190(3), pp. 355-366 (1999).

Walunas, et al., "CTLA-4 Can Function as a Negative Regulator of T Cell Activation", Immunity, vol. 1, pp. 405-413 (1994).

Robley, et al., "[36] Preparation of Tubulin from Brain", Methods Enzymology, vol. 85, pp. 376-385 (1982).

Stephens, et al., "The Evaluation of Combinations of Cytotoxic Drugs and Radiation: Isobolograms and Therapeutic Synergism", Rodent Tumor Models in Experimental Cancer Therapy, pp. 248-252, Pergamon Press, NY, Publ., Kallman, R.F., ed. (1987).

* cited by examiner

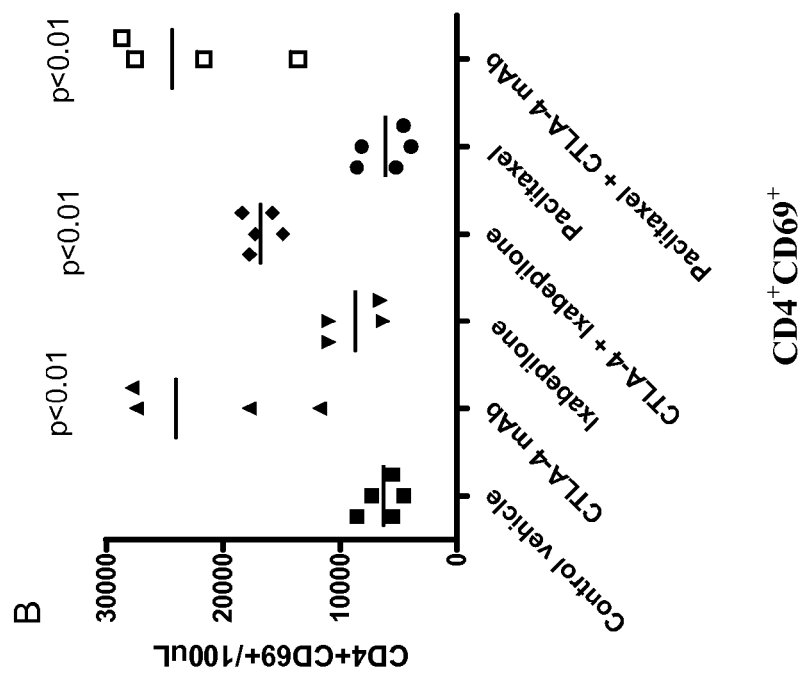
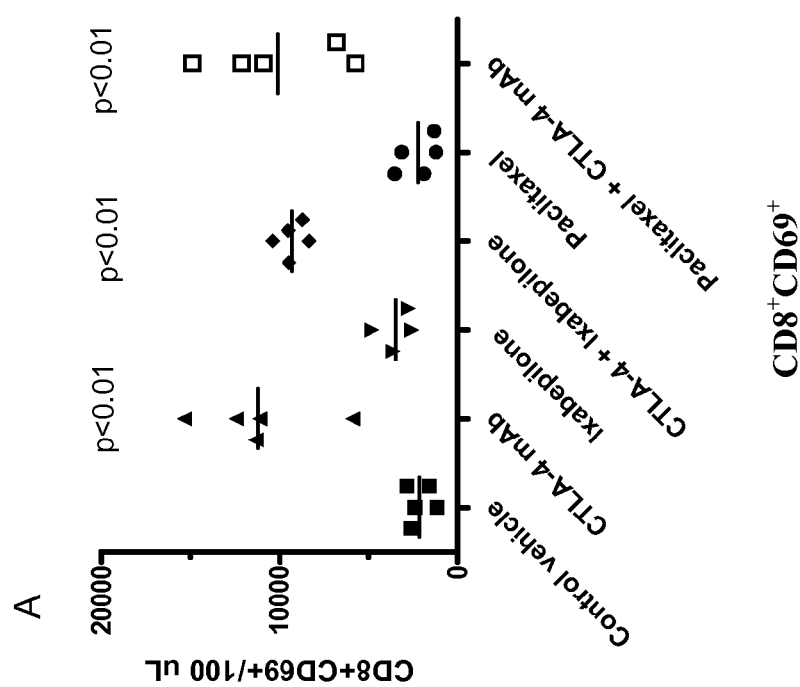
FIG. 4

SEQUENCE LISTING

```
<160> NUMBER OF SEQ ID NOS: 4

<210> SEQ ID NO 1
<211> LENGTH: 108
<212> TYPE: PRT
<213> ORGANISM: Homo sapiens

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Phe Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 2
<211> LENGTH: 118
<212> TYPE: PRT
<213> ORGANISM: Homo sapiens

<400> SEQUENCE: 2

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 3
<211> LENGTH: 9
<212> TYPE: PRT
<213> ORGANISM: Homo sapiens
```

```
<400> SEQUENCE: 3

Ile Met Asp Gln Val Pro Phe Ser Val
1               5

<210> SEQ ID NO 4
<211> LENGTH: 9
<212> TYPE: PRT
<213> ORGANISM: Homo sapiens

<400> SEQUENCE: 4

Tyr Leu Glu Pro Gly Pro Val Thr Val
1               5
```

COMBINATION OF ANTI-CTLA4 ANTIBODY WITH TUBULIN MODULATING AGENTS FOR THE TREATMENT OF PROLIFERATIVE DISEASES

This application claims benefit to International Application No. PCT/US2009/030291, filed Jan. 7, 2009 which, claims benefit to provisional application U.S. Ser. No. 61/019,778, filed Jan. 8, 2008; and to provisional application U.S. Ser. No. 61/056,957, filed May 29, 2008; under 35 U.S.C. 119(e). The entire teachings of the referenced applications are incorporated herein by reference.

FIELD OF THE INVENTION

This invention relates to the fields of oncology and improved therapy regimens.

BACKGROUND OF THE INVENTION

The National Cancer Institute has estimated that in the United States alone, 1 in 3 people will be struck with cancer during their lifetime. Moreover, approximately 50% to 60% of people contracting cancer will eventually succumb to the disease. The widespread occurrence of this disease underscores the need for improved anticancer regimens for the treatment of malignancy.

Due to the wide variety of cancers presently observed, numerous anticancer agents have been developed to destroy cancer within the body. These compounds are administered to cancer patients with the objective of destroying or otherwise inhibiting the growth of malignant cells while leaving normal, healthy cells undisturbed. Anticancer agents have been classified based upon their mechanism of action.

One type of chemotherapeutic is referred to as a metal coordination complex. It is believed this type of chemotherapeutic forms predominantly inter-strand DNA cross links in the nuclei of cells, thereby preventing cellular replication. As a result, tumor growth is initially repressed, and then reversed. Another type of chemotherapeutic is referred to as an alkylating agent. These compounds function by inserting foreign compositions or molecules into the DNA of dividing cancer cells. As a result of these foreign moieties, the normal functions of cancer cells are disrupted and proliferation is prevented. Another type of chemotherapeutic is an antineoplastic agent. This type of agent prevents, kills, or blocks the growth and spread of cancer cells. Still other types of anticancer agents include nonsteroidal aromastase inhibitors, bifunctional alkylating agents, etc.

Chemoimmunotherapy, the combination of chemotherapeutic and immunotherapeutic agents, is a novel approach for the treatment of cancer which combines the effects of agents that directly attack tumor cells producing tumor cell necrosis or apoptosis, and agents that modulate host immune responses to the tumor. Chemotherapeutic agents could enhance the effect of immunotherapy by generating tumor antigens to be presented by antigen-presenting cells creating a "polyvalent" tumor cell vaccine, and by distorting the tumor architecture, thus facilitating the penetration of the immunotherapeutic agents as well as the expanded immune population.

Ipilimumab is a human anti-human CTLA-4 antibody which blocks the binding of CTLA-4 to CD80 and CD86 expressed on antigen presenting cells and thereby, blocking the negative downregulation of the immune responses elicited by the interaction of these molecules. Since ipilimumab does not recognize mouse CTLA-4, an anti-mouse CTLA-4 antibody (clone UC10-4F10) was used in the studies presented herein to investigate the effect of CTLA-4 blockade with chemotherapeutic agents.

Microtubule-stabilizing agents, such as ixabepilone (IX-EMPRA™) and paclitaxel (TAXOL®), are commonly used for the treatment of many types of cancer and represent an attractive class of agents to combine with CTLA-4 blockade.

In the studies described herein the combination of microtubule-stabilizing agents and CTLA-4 blockade was investigated in several murine tumor models with different sensitivity to each agent.

The present inventors have discovered for the first time the synergistic benefit of combining a microtubule-modulating agent with an anti-CTLA-4 inhibitor for the treatment of proliferative diseases. It is an object of the invention to provide efficacious combination chemotherapeutic treatment regimens wherein one or more microtubule-modulating agents are combined with one or more anti-CTLA4 agents for the treatment of proliferative diseases.

SUMMARY OF THE INVENTION

The present invention provides a synergistic method for the treatment of anti-proliferative diseases, including cancer, which comprises administering to a mammalian species in need thereof a synergistically, therapeutically effective amount of: (1) at least one anti-proliferative agent and (2) an anti-CTLA4 antagonist.

A non-limiting example of an anti-proliferative agent would be a microtubule stabilizing agent, such as ixabepilone, other epothilones, and/or paclitaxel.

As is known in the art, ixabepilone refers to a compound having the following structure (I):

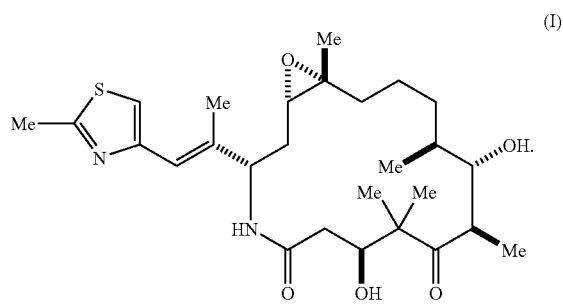

Compound (I) can also be referred to as (1S,3S,7S,10R,11S, 12S,16R)-7,11-dihydroxy-8,8,10,12,16-pentamethyl-3-[(1E)-1-methyl-2-(2-methyl-4-thiazolyl)ethenyl]-17-oxa-4-azabicyclo[14.1.0]heptadecane-5,9-dione in accordance with IUPAC nomenclature. Use of the term "(1S,3S,7S,10R, 11S,12S,16R)-7,11-dihydroxy-8,8,10,12,16-pentamethyl-3-[(1E)-1-methyl-2-(2-methyl-4-thiazolyl)ethenyl]-17-oxa-4-azabicyclo[14.1.0]heptadecane-5,9-dione" encompasses (unless otherwise indicated) solvates (including hydrates) and polymorphic forms of the compound (I) or its salts, such as the forms of (I) described in U.S. Pat. No. 6,605,599, issued Aug. 12, 2003, incorporated herein by reference in its entirety and for all purposes. Pharmaceutical compositions of (1S,3S, 7S,10R,11S,12S,16R)-7,11-dihydroxy-8,8,10,12,16-pentamethyl-3-[(1E)-1-methyl-2-(2-methyl-4-thiazolyl)ethenyl]-17-oxa-4-azabicyclo[14.1.0]heptadecane-5,9-dione include all pharmaceutically acceptable compositions comprising (1S,3S,7S,10R,11S,12S,16R)-7,11-dihydroxy-8,8, 10,12,16-pentamethyl-3-[(1E)-1-methyl-2-(2-methyl-4- thiazolyl)ethenyl]-17-oxa-4-azabicyclo[14.1.0]
heptadecane-5,9-dione and one or more diluents, vehicles and/or excipients One example of a pharmaceutical composition comprising (1S,3S,7S,10R,11S,12S,16R)-7,11-dihydroxy-8,8,10,12,16-pentamethyl-3-[(1E)-1-methyl-2-(2-methyl-4-thiazolyl)ethenyl]-17-oxa-4-azabicyclo[14.1.0]heptadecane-5,9-dione is IXEMPRA™ (Bristol-Myers Squibb Company). IXEMPRA™ comprises (1S,3S,7S,10R,11S,12S,16R)-7,11-dihydroxy-8,8,10,12,16-pentamethyl-3-[(1E)-1-methyl-2-(2-methyl-4-thiazolyl)ethenyl]-17-oxa-4-azabicyclo[14.1.0]heptadecane-5,9-dione as the active ingredient, also referred to as ixabepilone, for IV infusion including inactive ingredients in the form of a diluent consisting of a sterile, non-pyrogenic of 52.8% (w/v) purified polyoxyethylated castor oil and 39.8% (w/v) dehydrated alcohol, USP.

Non-limiting examples of other epothilones for use in the methods and compositions of the present invention are encompassed by formula II:

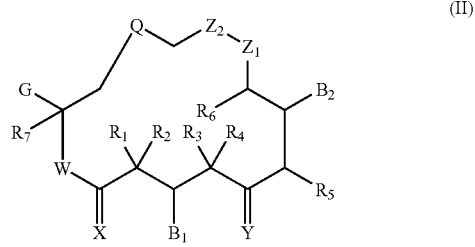

(II)

wherein:
Q is selected from the group consisting of:

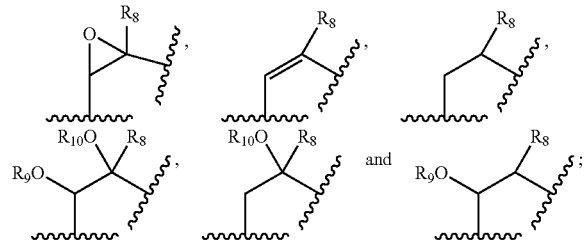

G is selected from the group consisting of alkyl, substituted alkyl, aryl, substituted aryl, heterocyclo,

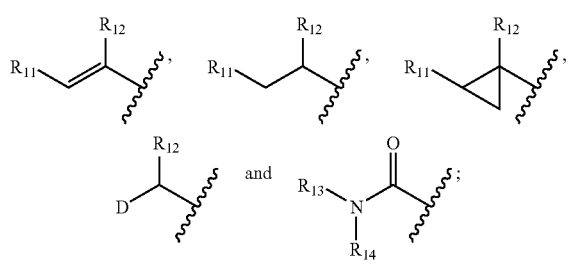

W is O or $NR_{15}$;
X is O or H, H;
Y is selected from the group consisting of O; H, $OR_{16}$; $OR_{17}$, $OR_{17}$; $NOR_{18}$; H, $NHOR_{19}$; H, $NR_{20}R_{21}$; H, H; and $CHR_{22}$; wherein $OR_{17}$, $OR_{17}$ can be a cyclic ketal;

$Z_1$ and $Z_2$ are independently selected from the group consisting of $CH_2$, O, $NR_{23}$, S, and $SO_2$, wherein only one of $Z_1$ and $Z_2$ can be a heteroatom;

$B_1$ and $B_2$ are independently selected from the group consisting of $OR_{24}$, $OCOR_{25}$, and O—C(=O)—$NR_{26}R_{27}$, and when $B_1$ is H and Y is OH, H, they can form a six-membered ring ketal or acetal;

D is selected from the group consisting of $NR_{28}R_{29}$, $NR_{30}COR_{31}$ and saturated heterocycle;

$R_1, R_2, R_3, R_4, R_5, R_6, R_7, R_{13}, R_{14}, R_{18}, R_{19}, R_{20}, R_{21}, R_{22}, R_{26}$ and $R_{27}$ are independently selected from the group consisting of H, alkyl, substituted alkyl, and aryl, and when $R_1$ and $R_2$ are alkyl can be joined to form a cycloalkyl, and when $R_3$ and $R_4$ are alkyl can be joined to form a cycloalkyl;

$R_9, R_{10}, R_{16}, R_{17}, R_{24}, R_{25}$ and $R_{31}$ are independently selected from the group consisting of H, alkyl, and substituted alkyl;

$R_8, R_{11}, R_{12}, R_{28}, R_{30}, R_{32}$, and $R_{33}$ are independently selected from the group consisting of H, alkyl, substituted alkyl, aryl, substituted aryl, cycloalkyl and heterocyclo; and $R_{15}, R_{23}$ and $R_{29}$ are independently selected from the group consisting of H, alkyl, substituted alkyl, aryl, substituted aryl, cycloalkyl, heterocyclo, $R_{32}$C=O, $R_{33}SO_2$, hydroxy, O-alkyl or O-substituted alkyl; and pharmaceutically acceptable salts thereof and any hydrates, solvates or geometric, optical and stereoisomers thereof.

Formula III provides another example of an epothilone suitable for use in the methods and compositions of the present invention:

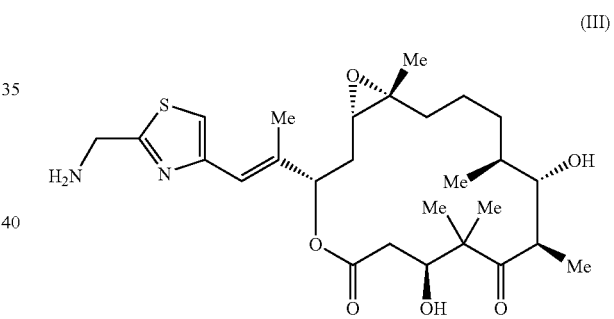

(III)

wherein:
P-Q is a C, C double bond or an epoxide;
G is

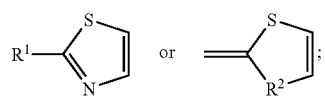

R is selected from the group of H, alkyl, and substituted alkyl;

$R^1$ is selected from the group consisting of:

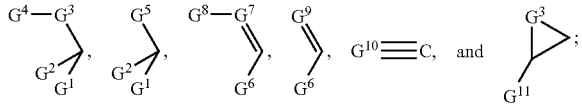

$R^2$ is

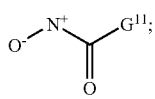

$G^1$ is selected from the group of H, halogen, CN, alkyl and substituted alkyl;

$G^2$ is selected from the group of H, alkyl, and substituted alkyl;

$G^3$ is selected from the group of O, S, and $NZ^1$;

$G^4$ is selected from the group of H, alkyl, substituted alkyl, $OZ^2$, $NZ^2Z^3$, $Z^2C=O$, $Z^4SO_2$, and optionally substituted glycosyl;

$G^5$ is selected from the group of halogen, $N_3$, NCS, SH, CN, NC, $N(Z^1)_3^+$ and heteroaryl;

$G^6$ is selected from the group of H, alkyl, substituted alkyl, $CF_3$, $OZ^5$, $SZ^5$, and $NZ^5Z^6$;

$G^7$ is $CZ^7$ or N;

$G^8$ is selected from the group of H, halogen, alkyl, substituted alkyl, $OZ^{10}$, $SZ^{10}$, $NZ^{10}Z^{11}$;

$G^9$ is selected from the group of O, S, —NH—NH— and —N=N—;

$G^{10}$ is N or $CZ^{12}$;

$G^{11}$ is selected from the group of $H_2N$, substituted $H_2N$, alkyl, substituted alkyl, aryl, and substituted aryl;

$Z^1$, $Z^6$, $Z^9$, and $Z^{11}$ are independently selected from the group H, alkyl, substituted alkyl, acyl, and substituted acyl;

$Z^2$ is selected from the group of H, alkyl, substituted alkyl, aryl, substituted aryl, and heterocycle;

$Z^3$, $Z^5$, $Z^8$, and $Z^{10}$ are independently selected from the group H, alkyl, substituted alkyl, acyl, substituted acyl, aryl, and substituted aryl;

$Z^4$ is selected from the group of alkyl, substituted alkyl, aryl, substituted aryl, and heterocycle;

$Z^7$ is selected from the group of H, halogen, alkyl, substituted alkyl, aryl, substituted aryl, $OZ^8$, $SZ^8$, and $NZ^8Z^9$; and $Z^{12}$ is selected from the group of H, halogen, alkyl, substituted alkyl, aryl, and substituted aryl;

with the proviso that when $R^1$ is

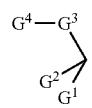

$G^1$, $G^2$, $G^3$ and $G^4$ cannot simultaneously have the following meanings:

$G^1$ and $G^2$=H, $G^3$=O and $G^4$=H or $Z^2C$=O where $Z^2$=alkyl group.

A preferred compound of Formula III of the invention is Formula IIIa:

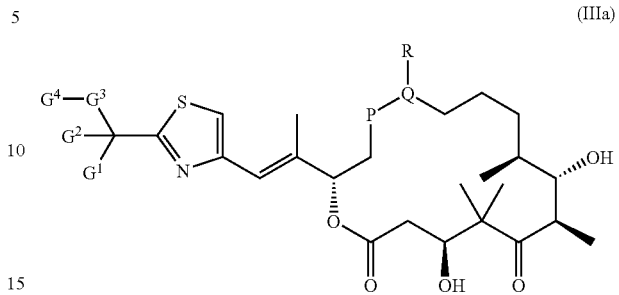

(IIIa)

wherein the symbols have the following meaning:
P-Q is a C,C double bond or an epoxide;
R is a H atom or a methyl group;
$G^1$ is an H atom, an alkyl group, a substituted alkyl group or a halogen atom;
$G^2$ is an H atom, an alkyl group or a substituted alkyl group;
$G^3$ is an O atom, an S atom or an $NZ^1$ group with $Z^1$ being an H atom, an alkyl group, a substituted alkyl group, an acyl group, or a substituted acyl group;
$G^4$ is an H atom, an alkyl group, a substituted alkyl group, an $OZ^2$ group, an $NZ^2Z^3$ group, a $Z^2C$=O group, a $Z^4SO_2$ group or an optionally substituted glycosyl group with $Z^2$ being a H atom, an alkyl group, a substituted alkyl group, an aryl group, a substituted aryl group or a heterocyclic group;
$Z^3$ an H atom, an alkyl group, a substituted alkyl group, an acyl group or a substituted acyl group; and
$Z^4$ an alkyl, a substituted alkyl, an aryl, a substituted aryl or a heterocyclic group, with the proviso that $G^1$, $G^2$, $G^3$ and $G^4$ cannot have simultaneously the following meanings: $G^1$ and $G^2$=H atom, $G^3$=O atom and $G^4$=H atom or $Z^2C$=O with $Z^2$=alkyl group.

A particularly preferred compound of Formula III is [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione (Compound 4) and pharmaceutically acceptable salts thereof.

As is known in the art, paclitaxel refers to a compound having the following structure (IV):

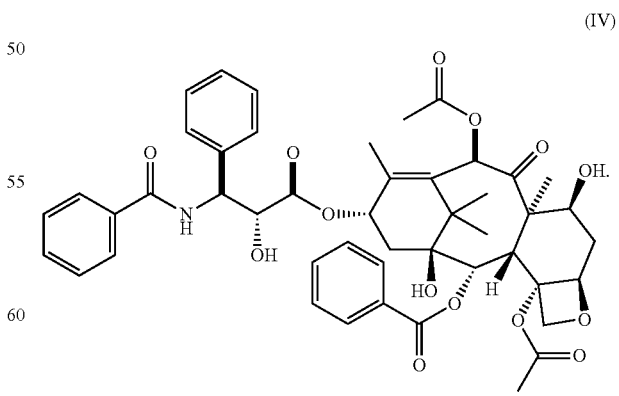

(IV)

Compound (IV) can also be referred to as 5beta,20-Epoxy-1,2alpha,4,7beta,10beta,13alpha-hexahydroxytax-11-en-9-one 4,10-diacetate 2-benzoate 13-ester with (2R,3S)—N- benzoyl-3-phenylisoserine in accordance with IUPAC nomenclature. Use of the term "5beta,20-Epoxy-1,2alpha,4,7beta,10beta,13alpha-hexahydroxytax-11-en-9-one 4,10-diacetate 2-benzoate 13-ester with (2R,3S)—N-benzoyl-3-phenylisoserine" encompasses (unless otherwise indicated) solvates (including hydrates) and polymorphic forms of the compound (IV) or its salts, such as the forms of (IV) described in U.S. Pat. No. 5,504,102, issued Apr. 2, 1996, incorporated herein by reference in its entirety and for all purposes. Pharmaceutical compositions of 5beta,20-Epoxy-1,2alpha,4,7beta,10beta,13alpha-hexahydroxytax-11-en-9-one 4,10-diacetate 2-benzoate 13-ester with (2R,3S)—N-benzoyl-3-phenylisoserine include all pharmaceutically acceptable compositions comprising 5beta,20-Epoxy-1,2alpha,4,7beta,10beta,13alpha-hexahydroxytax-11-en-9-one 4,10-diacetate 2-benzoate 13-ester with (2R,3S)—N-benzoyl-3-phenylisoserine and one or more diluents, vehicles and/or excipients. One example of a pharmaceutical composition comprising 5beta,20-Epoxy-1,2alpha,4,7beta,10beta,13alpha-hexahydroxytax-11-en-9-one 4,10-diacetate 2-benzoate 13-ester with (2R,3S)—N-benzoyl-3-phenylisoserine is TAXOL® (Bristol-Myers Squibb Company). TAXOL® comprises 5beta,20-Epoxy-1,2alpha,4,7beta,10beta,13alpha-hexahydroxytax-11-en-9-one 4,10-diacetate 2-benzoate 13-ester with (2R,3S)—N-benzoyl-3-phenylisoserine as the active ingredient, also referred to as paclitaxel, for IV infusion including inactive ingredients in the form of a diluent consisting of a sterile 0.9% Sodium Chloride injection, USP, 5% Dextrose Injection, USP, 0.9% Sodium Chloride and 5% Dextrose Injection, USP, or 5% Dextrose in Ringer's Injection to a final concentration of 0.3 to 1.2 mg/ml.

Suitable anti-proliferative agents for use in the methods of the invention, include, without limitation, taxanes, paclitaxel (paclitaxel is commercially available as TAXOL®), docetaxel, discodermolide (DDM), dictyostatin (DCT), Peloruside A, epothilones, epothilone A, epothilone B, epothilone C, epothilone D, epothilone E, epothilone F, furano-epothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discoderomolide, patupilone (EPO-906), KOS-862, KOS-1584, ZK-EPO, BMS-310705, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

The phrase "microtubulin modulating agent" is meant to refer to agents that either stabilize microtubulin or destabilize microtubulin synthesis and/or polymerization.

Suitable anti-CTLA4 antagonist agents for use in the methods of the invention, include, without limitation, anti-CTLA4 antibodies, human anti-CTLA4 antibodies, mouse anti-CTLA4 antibodies, mammalian anti-CTLA4 antibodies, humanized anti-CTLA4 antibodies, monoclonal anti-CTLA4 antibodies, polyclonal anti-CTLA4 antibodies, chimeric anti-CTLA4 antibodies, MDX-010 (ipilimumab), tremelimumab, anti-CD28 antibodies, anti-CTLA4 adnectins, anti-CTLA4 domain antibodies, single chain anti-CTLA4 fragments, heavy chain anti-CTLA4 fragments, light chain anti-CTLA4 fragments, inhibitors of CTLA4 that agonize the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP1212422B1. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014. Other anti-CTLA-4 antibodies that can be used in a method of the present invention include, for example, those disclosed in: WO 98/42752; U.S. Pat. Nos. 6,682,736 and 6,207,156; Hurwitz et al., *Proc. Natl. Acad. Sci. USA*, 95(17):10067-10071 (1998); Camacho et al., *J. Clin. Oncology*, 22(145):Abstract No. 2505 (2004) (antibody CP-675206); Mokyr et al., *Cancer Res*, 58:5301-5304 (1998), U.S. Pat. Nos. 5,977,318, 6,682,736, 7,109,003, and 7,132,281.

Additional anti-CTLA4 antagonists include, but are not limited to, the following: any inhibitor that is capable of disrupting the ability of CD28 antigen to bind to its cognate ligand, to inhibit the ability of CTLA4 to bind to its cognate ligand, to augment T cell responses via the co-stimulatory pathway, to disrupt the ability of B7 to bind to CD28 and/or CTLA4, to disrupt the ability of B7 to activate the co-stimulatory pathway, to disrupt the ability of CD80 to bind to CD28 and/or CTLA4, to disrupt the ability of CD80 to activate the co-stimulatory pathway, to disrupt the ability of CD86 to bind to CD28 and/or CTLA4, to disrupt the ability of CD86 to activate the co-stimulatory pathway, and to disrupt the co-stimulatory pathway, in general from being activated. This necessarily includes small molecule inhibitors of CD28, CD80, CD86, CTLA4, among other members of the co-stimulatory pathway; antibodies directed to CD28, CD80, CD86, CTLA4, among other members of the co-stimulatory pathway; antisense molecules directed against CD28, CD80, CD86, CTLA4, among other members of the co-stimulatory pathway; adnectins directed against CD28, CD80, CD86, CTLA4, among other members of the co-stimulatory pathway, RNAi inhibitors (both single and double stranded) of CD28, CD80, CD86, CTLA4, among other members of the co-stimulatory pathway, among other anti-CTLA4 antagonists.

Each of these references is specifically incorporated herein by reference for purposes of description of CTLA-4 antibodies. A preferred clinical CTLA-4 antibody is human monoclonal antibody 10D1 (also referred to as MDX-010 and ipilimumab and available from Medarex, Inc., Bloomsbury, N.J.) is disclosed in WO 01/14424.

Each of the anti-CTLA4 antagonist agents referenced herein may be administered either alone or in combination with a peptide antigen (e.g., gp100), either alone or in addition to an anti-proliferative agent disclosed herein.

The present invention further provides a pharmaceutical composition for the synergistic treatment of cancer which comprises a therapeutically effective amount of at least one (1) anti-proliferative agent and (2) an anti-CTLA4 antagonist.

In a preferred embodiment of the invention the anti-CTLA4 agent is administered simultaneous with or before or after the administration of a compound of Formulas I, II, III, IIIa, and/or IV or analogs thereof.

BRIEF DESCRIPTION OF THE DRAWINGS

FIG. 4 shows treatment with CTLA-4 mAb resulted in an increased number of $CD4^+$ and $CD8^+$ activated T cells ($CD4^+CD69^+$; $CD8^+CD69^+$), and that the addition of ixabepilone or paclitaxel to CTLA-4 mAb treatment did not alter the expansion of activated T cells elicited by CTLA-4 mAb treatment 2 days after treatment.

DETAILED DESCRIPTION OF THE INVENTION

Figure 1:
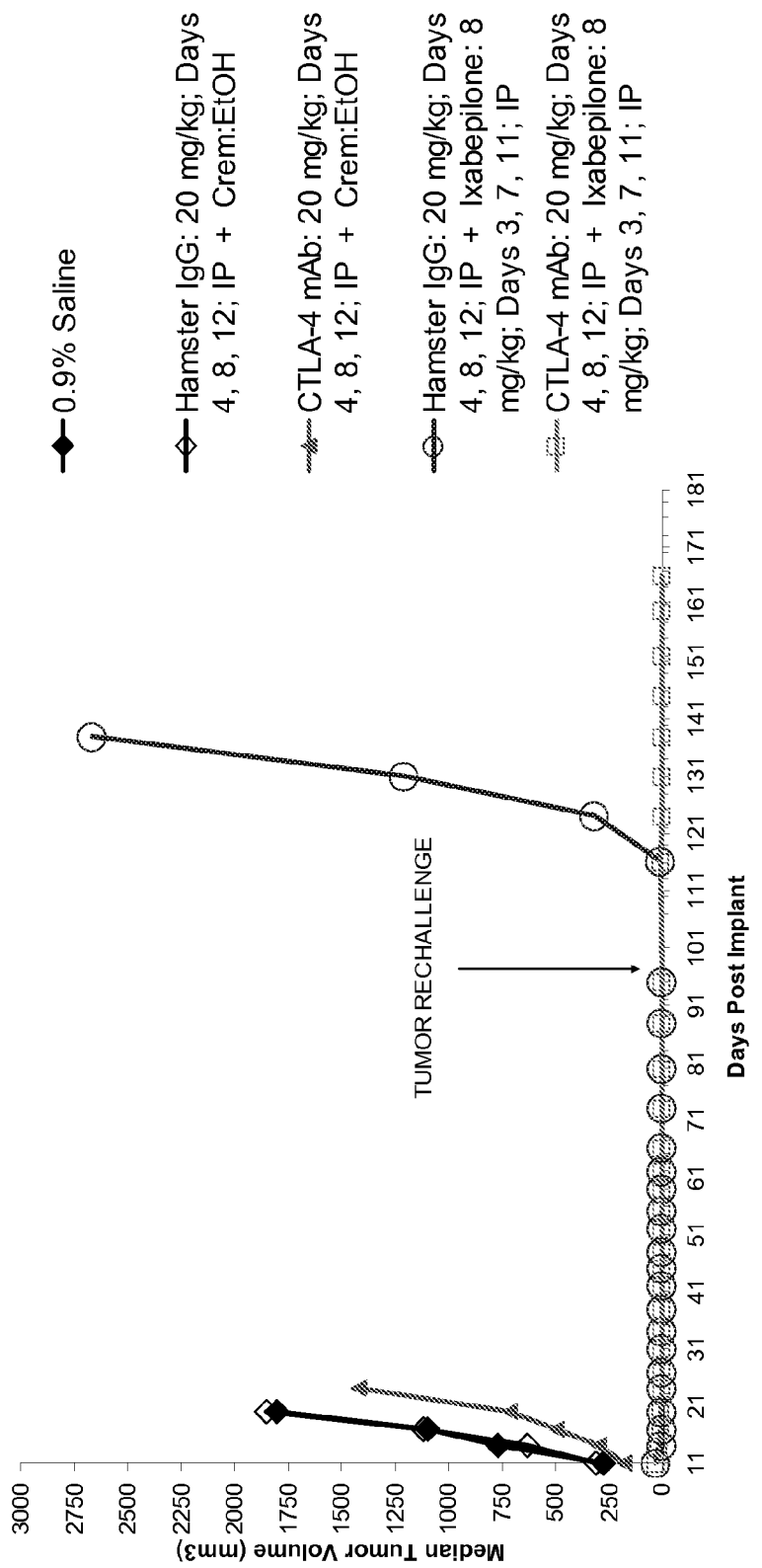
FIG. 1 shows the antitumor activity of CTLA-4 mAb in combination with ixabepilone in a murine M109 lung carcinoma tumor xenograft model. As shown, synergism was observed with the combination of anti-CTLA-4 antibody and ixabepilone.

In accordance with the present invention, methods for the scheduled administration of tubulin modulatory agents in synergistic combination(s) with at least one anti-CTLA4 agent for the treatment and prevention of proliferative diseases are provided.

Optimal T cell activation requires interaction between the T cell receptor and specific antigen (Bretscher, P. et al., *Science,* 169:1042-1049 (1970)) (the first signal) and engagement of costimulatory receptors on the surface of the T cell with costimulatory ligands expressed by the antigen-presenting cell (APC) (the second signal). Failure of the T cell to receive a second signal can lead to clonal anergy (Schwartz, R. H., *Science,* 248:1349-1356 (1990)). Two important T cell costimulatory receptors are CD28 and cytotoxic T lymphocyte-associated antigen 4 (CTLA-4, CD152) whose ligands on APC are B7-1 and B7-2 (Linsley, P. S. et al., *J. Exp. Med.,* 173:721-730 (1991); Linsley, P. S. et al., *J. Exp. Med.,* 174:561-569 (1991)). Although CD28 and CTLA-4 are closely related members of the Ig superfamily (Brunet, J. F. et al., *Nature,* 328:267-270 (1987)), they function antagonistically. CD28 is constitutively expressed on the surface of T cells (Gross, J. A. et al., *J. Immunol.,* 149:380-388 (1992)), and upon engagement with B7-1 or B7-2, enhances the T cell receptor-peptide-MHC signal to promote T cell activation, proliferation, and IL-2 production (Linsley, P. S. et al., *J. Exp. Med.,* 173:721-730 (1991); Alegre, M. L. et al., *Nat. Rev. Immunol* (2002)). CTLA-4 is not found on resting T cells but is up-regulated for 2-3 days after T cell activation (Lindsten, T. et al., *J. Immunol.,* 151:3489-3499 (1993), Walunas, T. L. et al., *Immunity,* 1:405-413 (1994)). CTLA-4 also binds to B7-1 and B7-2 but with greater affinity than CD28 (Linsley, P. S. et al., *Immunity,* 1:793-801 (1994)) and antagonizes T cell activation, interferes with IL-2 production and IL-2 receptor expression, and interrupts cell cycle progression of activated T cells (Walunas, T. L. et al., *J. Exp. Med.,* 183:2541-2550 (1996); Krummel, M. F. et al., *J. Exp. Med.,* 183:2533-2540 (1996); Brunner, M. C. et al., *J. Immunol.,* 162:5813-5820 (1999); Greenwald, R. J. et al., *Eur. J. Immunol.,* 32:366-373 (2002)). The overall T cell response is determined by the integration of all signals, stimulatory and inhibitory.

Because CTLA-4 appears to undermine T cell activation, attempts have been made to block CTLA-4 activity in murine models of cancer immunotherapy. In mice implanted with immunogenic tumors, administration of anti-CTLA-4 Ab enhanced tumor rejection (Leach, D. R. et al., *Science,* 271:1734-1736 (1996)), although little effect was seen with poorly immunogenic tumors such as SM1 mammary carcinoma or B16 melanoma. Enhanced antitumor immunity was seen when anti-CTLA-4 Ab was given with granulocyte-macrophage colony-stimulating factor (GM-CSF)-transduced B16 cell vaccine and was associated with depigmentation, suggesting that at least part of the antitumor response was antigen-specific against "self" melanocyte differentiation antigens (van Elsas, A. et al., *J. Exp. Med.,* 190:355-366 (1999); van Elsas, A. et al., *J. Exp. Med.,* 194:481-489 (2001)). In a transgenic murine model of primary prostate cancer, administrating anti-CTLA-4 Ab plus GM-CSF-expressing prostate cancer cells reduced the incidence and histological severity of prostate cancer and led to prostatitis in normal mice, again suggesting an antigen-specific immune response against self-antigens in tumor rejection (Hurwitz, A. A. et al., *Cancer Res.,* 60:2444-2448 (2000)). Furthermore, because many human tumor antigens are normal self-antigens, breaking tolerance against self may be critical to the success of cancer immunotherapy. The favorable tumor responses from CTLA-4 blockade in conjunction with tumor vaccines in murine models led to interest in using CTLA-4 blockade in human cancer immunotherapy.

Chemoimmunotherapy, the combination of chemotherapeutic and immunotherapeutic agents, is a novel approach for the treatment of cancer which combines the effects of agents that directly attack tumor cells producing tumor cell necrosis or apoptosis, and agents that modulate host immune responses to the tumor. Chemotherapeutic agents could enhance the effect of immunotherapy by generating tumor antigens to be presented by antigen-presenting cells creating a "polyvalent" tumor cell vaccine, and by distorting the tumor architecture, thus facilitating the penetration of the immunotherapeutic agents as well as the expanded immune population.

Microtubulin modulatory agents either agonize or inhibit a cells ability to maintain proper microtubulin assemblies. In the case of paclitaxel (marketed as TAXOL®) causes mitotic abnormalities and arrest, and promotes microtubule assembly into calcium-stable aggregated structures resulting in inhibition of cell replication.

Epothilones mimic the biological effects of TAXOL®, (Bollag et al., *Cancer Res.,* 55:2325-2333 (1995), and in competition studies act as competitive inhibitors of TAXOL® binding to microtubules. However, epothilones enjoy a significant advantage over TAXOL® in that epothilones exhibit a much lower drop in potency compared to TAXOL® against a multiple drug-resistant cell line (Bollag et al. (1995)). Furthermore, epothilones are considerably less efficiently exported from the cells by P-glycoprotein than is TAXOL® (Gerth et al. (1996)).

Ixabepilone is a semi-synthetic lactam analogue of patupilone that binds to tubulin and promotes tubulin polymerisation and microtubule stabilisation, thereby arresting cells in the G2/M phase of the cell cycle and inducing tumour cell apoptosis.

Thus, in a preferred embodiment, the therapeutic method of the invention comprises the administration of Formulas I, II, III, IIIa, and/or IV or analogs thereof in combination with one or more anti-CTLA4 agent(s). The anti-proliferative agent disclosed herein, when used in combination with at least one anti-CTLA4 agent(s) demonstrate superior cytotoxic/anti-tumor activity.

A preferred epothilone analog for use in the methods of the invention is a compound of Formula II:

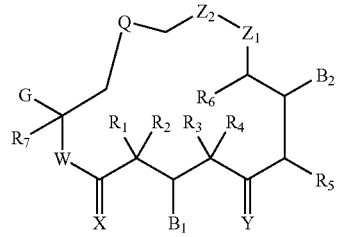

(II)

wherein:
Q is selected from the group consisting of:

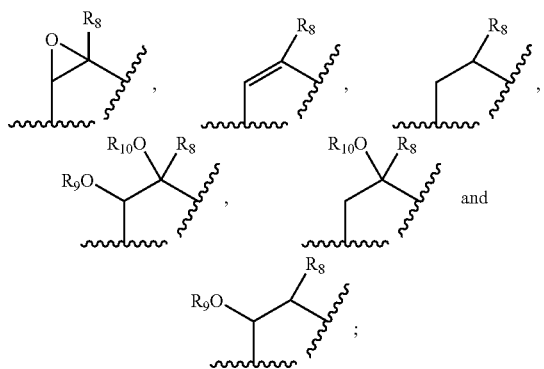

G is selected from the group consisting of alkyl, substituted alkyl, aryl, substituted aryl, heterocyclo,

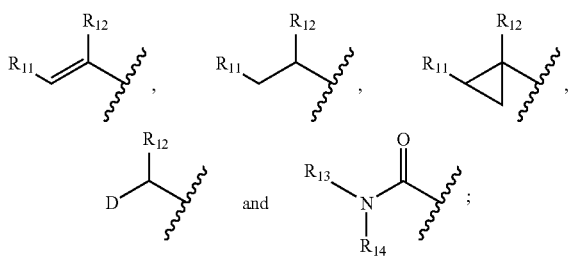

W is O or $NR_{15}$;
X is O or H, H;
Y is selected from the group consisting of O; H, $OR_{16}$; $OR_{17}$, $OR_{17}$; $NOR_{18}$; H, $NHOR_{19}$; H, $NR_{20}R_{21}$; H, H; and $CHR_{22}$; wherein $OR_{17}$, $OR_{17}$ can be a cyclic ketal;
$Z_1$ and $Z_2$ are independently selected from the group consisting of $CH_2$, O, $NR_{23}$, S, and $SO_2$, wherein only one of $Z_1$ and $Z_2$ can be a heteroatom;
$B_1$ and $B_2$ are independently selected from the group consisting of $OR_{24}$, $OCOR_{25}$, and O—C(=O)—$NR_{26}R_{27}$, and when $B_1$ is H and Y is OH, H, they can form a six-membered ring ketal or acetal;
D is selected from the group consisting of $NR_{28}R_{29}$, $NR_{30}COR_{31}$ and saturated heterocycle;
$R_1$, $R_2$, $R_3$, $R_4$, $R_5$, $R_6$, $R_7$, $R_{13}$, $R_{14}$, $R_{18}$, $R_{19}$, $R_{20}$, $R_{21}$, $R_{22}$, $R_{26}$ and $R_{27}$ are independently selected from the group consisting of H, alkyl, substituted alkyl, and aryl, and when $R_1$ and $R_2$ are alkyl can be joined to form a cycloalkyl, and when $R_3$ and $R_4$ are alkyl can be joined to form a cycloalkyl;
$R_9$, $R_{10}$, $R_{16}$, $R_{17}$, $R_{24}$, $R_{25}$ and $R_{31}$ are independently selected from the group consisting of H, alkyl, and substituted alkyl;
$R_8$, $R_{11}$, $R_{12}$, $R_{28}$, $R_{30}$, $R_{32}$, and $R_{33}$ are independently selected from the group consisting of H, alkyl, substituted alkyl, aryl, substituted aryl, cycloalkyl and heterocyclo;
$R_{15}$, $R_{23}$ and $R_{29}$ are independently selected from the group consisting of H, alkyl, substituted alkyl, aryl, substituted aryl, cycloalkyl, heterocyclo, $R_{32}$C=O, $R_{33}SO_2$, hydroxy, O-alkyl or O-substituted alkyl; and
pharmaceutically acceptable salts thereof and any hydrates, solvates or geometric, optical and stereoisomers thereof.

Another preferred epothilone for use in the present invention is a compound of Formula III:

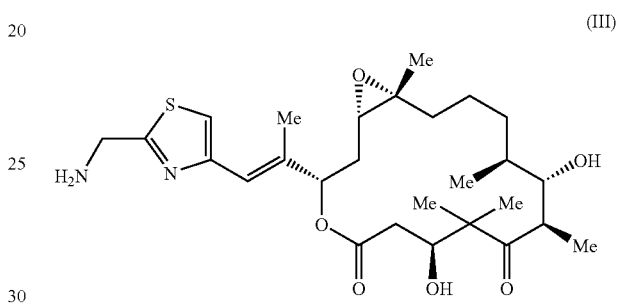

(III)

wherein:
P-Q is a C, C double bond or an epoxide;
G is

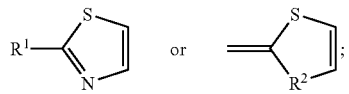

R is selected from the group of H, alkyl, and substituted alkyl;
$R^1$ is selected from the group consisting of:

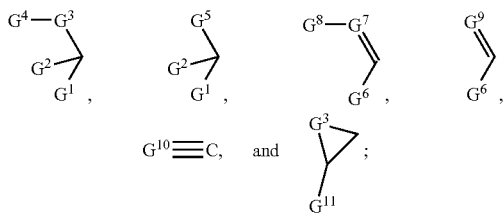

$R^2$ is

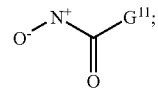

$G^1$ is selected from the group of H, halogen, CN, alkyl and substituted alkyl;
$G^2$ is selected from the group of H, alkyl, and substituted alkyl;

$G^3$ is selected from the group of O, S, and $NZ^1$;

$G^4$ is selected from the group of H, alkyl, substituted alkyl, $OZ^2$, $NZ^2Z^3$, $Z^2C=O$, $Z^4SO_2$, and optionally substituted glycosyl;

$G^5$ is selected from the group of halogen, $N_3$, NCS, SH, CN, NC, $N(Z^1)_3^+$ and heteroaryl;

$G^6$ is selected from the group of H, alkyl, substituted alkyl, $CF_3$, $OZ^5$, $SZ^5$, and $NZ^5Z^6$;

$G^7$ is $CZ^7$ or N;

$G^8$ is selected from the group of H, halogen, alkyl, substituted alkyl, $OZ^{10}$, $SZ^{10}$, $NZ^{10}Z^{11}$;

$G^9$ is selected from the group of O, S, —NH—NH— and —N=N—;

$G^{10}$ is N or $CZ^{12}$;

$G^{11}$ is selected from the group of $H_2N$, substituted $H_2N$, alkyl, substituted alkyl, aryl, and substituted aryl;

$Z^1$, $Z^6$, $Z^9$, and $Z^{11}$ are independently selected from the group H, alkyl, substituted alkyl, acyl, and substituted acyl;

$Z^2$ is selected from the group of H, alkyl, substituted alkyl, aryl, substituted aryl, and heterocycle;

$Z^3$, $Z^5$, $Z^8$, and $Z^{10}$ are independently selected from the group H, alkyl, substituted alkyl, acyl, substituted acyl, aryl, and substituted aryl;

$Z^4$ is selected from the group of alkyl, substituted alkyl, aryl, substituted aryl, and heterocycle;

$Z^7$ is selected from the group of H, halogen, alkyl, substituted alkyl, aryl, substituted aryl, $OZ^8$, $SZ^8$, and $NZ^8Z^9$; and $Z^{12}$ is selected from the group of H, halogen, alkyl, substituted alkyl, aryl, and substituted aryl;

with the proviso that when $R^1$ is

$G^1$, $G^2$, $G^3$ and $G^4$ cannot simultaneously have the following meanings:

$G^1$ and $G^2$=H, $G^3$=O and $G^4$=H or $Z^2C=O$ where $Z^2$=alkyl group.

A preferred compound of Formula III of the invention is Formula IIIa:

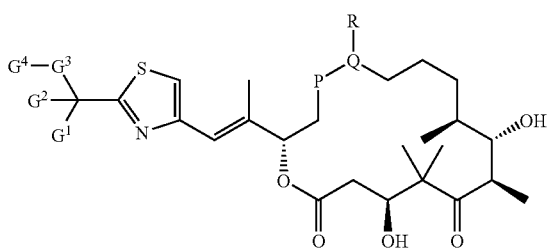

(IIIa)

wherein the symbols have the following meaning:

P-Q is a C,C double bond or an epoxide;

R is a H atom or a methyl group;

$G^1$ is an H atom, an alkyl group, a substituted alkyl group or a halogen atom;

$G^2$ is an H atom, an alkyl group or a substituted alkyl group;

$G^3$ is an O atom, an S atom or an $NZ^1$ group with $Z^1$ being an H atom, an alkyl group, a substituted alkyl group, an acyl group, or a substituted acyl group, and $G^4$ is an H atom, an alkyl group, a substituted alkyl group, an $OZ^2$ group, an $NZ^2Z^3$ group, a $Z^2C=O$ group, a $Z^4SO_2$ group or an optionally substituted glycosyl group with $Z^2$ being a H atom, an alkyl group, a substituted alkyl group, an aryl group, a substituted aryl group or a heterocyclic group;

$Z^3$ an H atom, an alkyl group, a substituted alkyl group, an acyl group or a substituted acyl group; and $Z^4$ an alkyl, a substituted alkyl, an aryl, a substituted aryl or a heterocyclic group, with the proviso that $G^1$, $G^2$, $G^3$ and $G^4$ cannot have simultaneously the following meanings: $G^1$ and $G^2$=H atom, $G^3$=O atom and $G^4$=H atom or $Z^2C=O$ with $Z^2$=alkyl group.

A particularly preferred compound of Formula III is [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione (Compound 4) and pharmaceutically acceptable salts thereof.

When describing the compounds of the present invention, the phrase "lower alkyl" or "lower alk" (as part of another group) refers to an unsubstituted alkyl group of 1 to 6, preferably 1 to 4, carbon atoms.

The term "aralkyl" refers to an aryl group bonded directly through a lower alkyl group. A preferred aralkyl group is benzyl.

The term "aryl" refers to a monocyclic or bicyclic aromatic hydrocarbon group having 6 to 12 carbon atoms in the ring portion. Exemplary of aryl herein are phenyl, naphthyl and biphenyl groups.

The term "heterocyclo" refers to a fully saturated or unsaturated, aromatic or nonaromatic cyclic group which is a 4 to 7 membered monocyclic, 7 to 11 membered bicyclic, or 10 to 15 membered tricyclic ring system which has at least one heteroatom in at least one carbon atom-containing ring. Each ring of the heterocyclic group containing a heteroatom may have 1, 2, 3 or 4 heteroatoms selected from nitrogen, oxygen and sulfur where the nitrogen and sulfur heteroatoms may also optionally be oxidized and the nitrogen heteroatoms may also optionally be quaternized. The heterocyclo group may be attached at any heteroatom or carbon atom.

Exemplary monocyclic heterocyclo groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane, tetrahydro-1,1-dioxothienyl, dioxanyl, isothiazolidinyl, thietanyl, thiiranyl, triazinyl, triazolyl, and the like.

Exemplary bicyclic heterocyclo groups include benzothiazolyl, benzoxazolyl, benzothienyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

When a group is referred to as being optionally substituted, it may be substituted with one to five, preferably one to three, substituents such as F, Cl, Br, I, trifluoromethyl, trifluoromethoxy, hydroxy, lower alkoxy, cycloalkoxy, heterocyclooxy, oxo, lower alkanoyl, aryloxy, lower alkanoyloxy, amino, lower alkylamino, arylamino, aralkylamino, cycloalkylamino, heterocycloamino, disubstituted amines in which the two amino substituents independently are selected from lower alkyl, aryl or aralkyl, lower alkanoylamino, aroylamino, aralkanoylamino, substituted lower alkanoylamino, substituted arylamino, substituted aralkylanoylamino, thiol, lower alkylthio, arylthio, aralkylthio, cycloalkylthio, heterocyclothio, lower alkylthiono, arylthiono, aralkylthiono, lower alkylsulfonyl, arylsulfonyl, aralkylsulfonyl, sulfonamide (e.g., SO$_2$NH$_2$), substituted sulfonamide, nitro, cyano, carboxy, carbamyl (e.g., CONH$_2$), substituted carbamyl (e.g., CONH-lower alkyl, CONH-aryl, CONH-aralkyl or cases where there are two substituents on the nitrogen independently selected from lower alkyl, aryl or aralkyl), lower alkoxycarbonyl, aryl, substituted aryl, guanidino, and heterocyclos (e.g., indolyl, imidazolyl, furyl, thienyl, thiazolyl, pyrrolidyl, pyridyl, pyrimidyl and the like). Where noted above that the substituent is further substituted, it will be substituted with F, Cl, Br, I, optionally substituted lower alkyl, hydroxy, optionally substituted lower alkoxy, optionally substituted aryl, or optionally substituted aralkyl.

All stereoisomers of the Formula I, II, III, IIIa and IV compounds of the instant invention are contemplated, either in admixture or in pure or substantially pure form. The definition of the formula I compounds embraces all possible stereoisomers and their mixtures. The Formula I, II, III, IIIa and IV definitions very particularly embrace the racemic forms and the isolated optical isomers having the specified activity.

A particularly preferred epothilone analog for use in the methods of the invention is Compound 1: [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione. Another exemplary epothilone is [1S-[1R*,3R* (E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione, Compound 4.

Compound 1, an exemplary epothilone analog of the invention, is a semi-synthetic epothilone analog and has a mode of action analogous to paclitaxel (i.e., microtubule stabilization). However, in preclinical pharmacology studies, Compound 1 has demonstrated significant improvement over paclitaxel in several critical aspects. Compound 1 exhibits a very impressive and broad spectrum of antitumor activity against paclitaxel-sensitive (A2780, HCT116 and LS174T) and, more importantly, as well as paclitaxel-resistant human colon tumors (HCT116NM46), ovarian carcinoma (Pat-7 and A2780Tax) and breast carcinoma (Pat-21) models. Compound 1 is orally efficacious; the antitumor activity produced after oral administration is comparable to that produced by parenteral administration of the drug. These preclinical efficacy data indicate that Compound 1 demonstrates improved clinical efficacy in TAXOL®-insensitive and sensitive disease types.

Compound 2: (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile, hydrochloride salt Compound 3: A CDK inhibitor is shown below

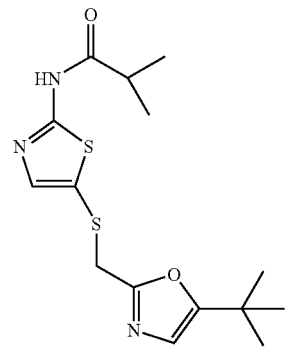 [SMILES: CC(C)C(=O)Nc1ncc(SCc2ncc(C(C)(C)C)o2)s1]

Compound 4: 1S-[1R*,3R*(E),7R*,10S*,11R*,12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione.

Compound 5: N-[5-[[[5-(1,1-Dimethylethyl)-2-oxazolyl]methyl]thio]-2-thiazolyl]-4-piperidinecarboxamide.

In a preferred embodiment of the invention a compound of Formulas I, II, III, IIIa, and/or IV or analogs thereof administered in conjunction with at least one anti-CTLA-4 agent.

The combination of at least one anti-proliferative compound with at least one anti-CTLA4 agent, may also include the addition of an anti-proliferative cytotoxic agent. Classes of compounds that may be used as anti-proliferative cytotoxic agents include the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as TAXOL®), Mithramycin, Deoxyco-formycin, Mitomycin-C, L-Asparaginase, Interferons (especially IFN-a), Etoposide, and Teniposide.

Other anti-proliferative cytotoxic agents are navelbene, CPT-11, anastrazole, letrazole, capecitabine, reloxafine, cyclophosphamide, ifosamide, and droloxafine.

The combination of at least one anti-proliferative compound with at least one anti-CTLA4 agent, may also include the addition of an anti-proliferative cytotoxic agent either alone or in combination with radiation therapy.

Other combinations with the at least one anti-CTLA4 agent may include a combination of another co-stimulatory pathway agonist (i.e., immunostimulant), a tubulin stabilizing agent (e.g., pacitaxol, epothilone, taxane, etc.), IXEMPRA™, Dacarbazine, Paraplatin, Docetaxel, one or more peptide vaccines, MDX-1379 Melanoma Peptide Vaccine, one or more gp100 peptide vaccine, fowlpox-PSA-TRICOM™ vaccine, vaccinia-PSA-TRICOM™ vaccine, MART-1 antigen, sargramostim, ticilimumab, Combination Androgen Ablative Therapy; the combination of ipilimumab and another co-stimulatory pathway agonist; combination of ipilimumab and a tubulin stabilizing agent (e.g., pacitaxol, epothilone, taxane, etc.); combination of ipilimumab and IXEMPRA™, the combination of ipilimumab with Dacarbazine, the combination of ipilimumab with Paraplatin, the combination of ipilimumab with Docetaxel, the combination of ipilimumab with one or more peptide vaccines, the combination of ipilimumab with MDX-1379 Melanoma Peptide Vaccine, the combination of ipilimumab with one or more gp100 peptide vaccine, the combination of ipilimumab with fowlpox-PSA-TRICOM™ vaccine, the combination of ipilimumab with vaccinia-PSA-TRICOM™ vaccine, the combination of ipilimumab with MART-1 antigen, the combination of ipilimumab with sargramostim, the combination of ipilimumab with ticilimumab, and/or the combination of ipilimumab with Combination Androgen Ablative Therapy. The combinations of the present invention may also be used in conjunction with other well known therapies that are selected for their particular usefulness against the condition that is being treated.

Other co-stimulatory pathway modulators of the present invention that may be used alone or in combination with other co-stimulatory pathway modulators disclosed herein, or in combination with other compounds disclosed herein include, but are not limited to, the following: agatolimod, belatacept, blinatumomab, CD40 ligand, anti-B7-1 antibody, anti-B7-2 antibody, anti-B7-H4 antibody, AG4263, eritoran, anti-OX40 antibody, ISF-154, and SGN-70.

The phrase "radiation therapy" includes, but is not limited to, x-rays or gamma rays which are delivered from either an externally applied source such as a beam or by implantation of small radioactive sources.

As referenced herein, the at least one anti-proliferative agent may be a microtubule affecting agent. A microtubule affecting agent interferes with cellular mitosis and are well known in the art for their anti-proliferative cytotoxic activity. Microtubule affecting agents useful in the invention include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (TAXOL®, NSC 125973), TAXOL® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (disclosed in U.S. Pat. No. 6,262,094, issued Jul. 17, 2001), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione (disclosed in U.S. Ser. No. 09/506,481 filed on Feb. 17, 2000, and examples 7 and 8 herein), and derivatives thereof; and other microtubule-disruptor agents. Additional antineoplastic agents include, discodermolide (see Service, *Science*, 274: 2009 (1996)) estramustine, nocodazole, MAP4, and the like. Examples of such agents are also described in the scientific and patent literature, see, e.g., Bulinski, *J. Cell Sci.*, 110: 3055-3064 (1997); Panda, *Proc. Natl. Acad. Sci. USA*, 94:10560-10564 (1997); Muhlradt, *Cancer Res.*, 57:3344-3346 (1997); Nicolaou, *Nature*, 387:268-272 (1997); Vasquez, *Mol. Biol. Cell.*, 8:973-985 (1997); Panda, *J. Biol. Chem.*, 271:29807-29812 (1996).

In cases where it is desirable to render aberrantly proliferative cells quiescent in conjunction with or prior to treatment with the chemotherapeutic methods of the invention, hormones and steroids (including synthetic analogs): 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex can also be administered to the patient.

Also suitable for use in the combination chemotherapeutic methods of the invention are antiangiogenics such as matrix metalloproteinase inhibitors, and other VEGF inhibitors, such as anti-VEGF antibodies and small molecules such as ZD6474 and SU6668 are also included. Anti-Her2 antibodies from Genentech may also be utilized. A suitable EGFR inhibitor is EKB-569 (an irreversible inhibitor). Also included are Imclone antibody C225 immunospecific for the EGFR, and src inhibitors.

Also suitable for use as an antiproliferative cytostatic agent is CASODEX® which renders androgen-dependent carcinomas non-proliferative. Yet another example of a cytostatic agent is the antiestrogen Tamoxifen which inhibits the proliferation or growth of estrogen dependent breast cancer. Inhibitors of the transduction of cellular proliferative signals are cytostatic agents. Examples are epidermal growth factor inhibitors, Her-2 inhibitors, MEK-1 kinase inhibitors, MAPK kinase inhibitors, PI3 inhibitors, Src kinase inhibitors, and PDGF inhibitors.

As mentioned, certain anti-proliferative agents are anti-angiogenic and antivascular agents and, by interrupting blood flow to solid tumors, render cancer cells quiescent by depriving them of nutrition. Castration, which also renders androgen dependent carcinomas non-proliferative, may also be utilized. Starvation by means other than surgical disruption of blood flow is another example of a cytostatic agent. A particularly preferred class of antivascular cytostatic agents is the combretastatins. Other exemplary cytostatic agents include MET kinase inhibitors, MAP kinase inhibitors, inhibitors of non-receptor and receptor tyrosine kinases, inhibitors of integrin signaling, and inhibitors of insulin-like growth factor receptors.

Thus, the present invention provides methods for the synergistic treatment of a variety of cancers, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, bone cancer, bone tumors, adult malignant fibrous histiocytoma of bone; childhood malignant fibrous histiocytoma of bone, sarcoma, pediatric sarcoma, sinonasal natural killer, neoplasms, plasma cell neoplasm; myelodysplastic syndromes; neuroblastoma; testicular germ cell tumor, intraocular melanoma, myelodysplastic syndromes; myelodysplastic/myeloproliferative diseases, synovial sarcoma, chronic myeloid leukemia, acute lymphoblastic leukemia, philadelphia chromosome positive acute lymphoblastic leukemia (Ph+ ALL), multiple myeloma, acute myelogenous leukemia, chronic lymphocytic leukemia, mastocytosis and any symptom associated with mastocytosis, and any metastasis thereof. In addition, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, mast cell leukemia, in addition to other cancers. Other cancers are also included within the scope of disorders including, but are not limited to, the following: carcinoma, including that of the bladder, urothelial carcinoma, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma, and any metastasis thereof.

Most preferably, the invention is used to treat accelerated or metastatic cancers of the bladder, pancreatic cancer, prostate cancer, non-small cell lung cancer, colorectal cancer, and breast cancer.

In a preferred embodiment of this invention, a method is provided for the synergistic treatment of cancerous tumors. Advantageously, the synergistic method of this invention reduces the development of tumors, reduces tumor burden, or produces tumor regression in a mammalian host.

Methods for the safe and effective administration of most of these chemotherapeutic agents are known to those skilled in the art. In addition, their administration is described in the standard literature.

For example, the administration of many of the chemotherapeutic agents is described in the *Physicians' Desk Reference* (PDR), e.g., 1996 edition (Medical Economics Company, Montvale, N J 07645-1742, USA); the disclosure of which is incorporated herein by reference thereto.

Preferred compounds of Formula II for use in the methods of the present invention include:

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4,13,17-trioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-4,13,17-trioxabicyclo[14.1.0]heptadecane-5,9-dione;

[4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-1,10-dioxa-13-cyclohexadecene-2,6-dione;

[4S-[4R*,7S*,8R*,9R*,15R*(E)]]-4,8-dihydroxy-5,5,7,9-tetramethyl-16-[1-methyl-2-(2-methyl-4-thiazolyl)ethenyl]-1,10-dioxa-13-cyclohexadecene-2,6-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4,14,17-trioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-4,14,17-trioxabicyclo[14.1.0]heptadecane-5,9-dione;

[4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-1,11-dioxa-13-cyclohexadecene-2,6-dione;

[4S-[4R*,7S*,8R*,9R*,15R*(E)]]-4,8-dihydroxy-5,5,7,9-tetramethyl-16-[1-methyl-2-(2-methyl-4-thizolyl)ethenyl]-1,11-dioxa-13-cyclohexadecene-2,6-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4,17-dioxabicyclo[14.1.0]heptadecane-9-one;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-4,17-dioxabicyclo[14.1.0]heptadecane-9-one;

[1S-[1R*,3R*(E),7R*,10S*,11R*,12R*,16S*]]-7,11-dihydroxy-3,8,8,10,12,16-hexamethyl-3-[1-methyl-2-(2-methyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-dihydroxy-3,8,8,10,12-pentamethyl-3-[1-methyl-2-(2-methyl-4-thiazolyl)ethenyl]-4,17-dioxabicyclo[14.1.0]heptadecane-5,9-dione;

[4S-[4R*,7S*,8R*,9R*,15R*(E)]]-4,8-dihydroxy-5,5,7,9,13,16-hexamethyl-16-[1-methyl-2-(2-methyl-4-thiazolyl)ethenyl]-1-oxa-13-cyclohexadecene-2,6-dione;

[4S-[4R*,7S*,8R*,9R*,15R*(E)]]-4,8-dihydroxy-5,5,7,9,16-pentamethyl-16-[1-methyl-2-(2-methyl-4-thiazolyl)ethenyl]-1-oxa-13-cyclohexadecene-2,6-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-dihydroxy-6,8,8,10,12-pentamethyl-3-[1-methyl-2-(2-methyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-4-aza-17-oxabicyclo[14.1.0]heptadecane-5,9-dione;

[4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-1-aza-13-cyclohexadecene-2,6-dione;

[4S-[4R*,7S*,8R*,9R*,15R*(E)]]-4,8-dihydroxy-5,5,7,9-tetramethyl-16-methyl-2-(2-methyl-4-thiazolyl)ethenyl]-1-aza-13-cyclohexadecene-2,6-dione;

[1S-[1R*,3R*(E),7R*,10S*,11R*,12R*,16S*]]-7,11-dihydroxy-4,8,8,10,12,16-hexamethyl-3-[1-methyl-2-(2-methyl-4-thiazolyl)ethenyl]-4-aza-17-oxabicyclo[14.1.0]heptadecane-5,9-dione;

[1S-[1R*,3R*(E),7R*,10S*,11R*,12R*,16S*]]-7,11-dihydroxy-4,8,8,10,12-pentamethyl-3-[1-methyl-2-(2-methyl-4-thiazolyl)ethenyl]-4-aza-17-oxabicyclo[14.1.0]heptadecane-5,9-dione;

[4S-[4R*,7S*,8R*,9R*,15R*(E)]]-4,8-dihydroxy-1,5,5,7,9,13-hexamethyl-16-[1-methyl-2-(2-methyl-4-thiazolyl)ethenyl]-1-aza-13-cyclohexadecene-2,6-dione;

[4S-[4R*,7S*,8R*,9R*,15R*(E)]]-4,8-dihydroxy-1,5,5,7,9-pentamethyl-16-[1-methyl-2-(2-methyl-4-thiazolyl)ethenyl]-1-aza-13-cyclohexadecene-2,6-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-13-aza-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-13-aza-4,17-dioxabicyclo[14.1.0]heptadecane-5,9-dione;

[4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-10-aza-1-oxa-13-cyclohexadecene-2,6-dione;

[4S-[4R*,7S*,8R*,9R*,15R*(E)]]-4,8-dihydroxy-5,5,7,9-tetramethyl-16-methyl-2-(2-methyl-4-thiazolyl)ethenyl]-10-aza-1-oxa-13-cyclohexadecene-2,6-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-14-aza-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-14-aza-4,17-dioxabicyclo[14.1.0]heptadecane-5,9-dione;

[4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-11-aza-1-oxa-13-cyclohexadecene-2,6-dione;

[4S-[4R*,7S*,8R*,9R*,15R*(E)]]-4,8-dihydroxy-5,5,7,9-tetramethyl-16-[1-methyl-2-(2-methyl-4-thiazolyl)ethenyl]-11-aza-1-oxa-13-cyclohexadecene-2,6-dione;

[1S-[1R*,3R*,7R*,10S*,11R*,12R*,16S*]]-N-phenyl-7,11-dihydroxy-8,8,10,12,16-pentamethyl-5,9-dioxo-4,17-dioxabicyclo[14.1.0]heptadecane-3-carboxamide;

[1S-[1R*,3R*,7R*,10S*,11R*,12R*,16S*]]-N-phenyl-7,11-dihydroxy-8,8,10,12-tetramethyl-5,9-dioxo-4,17-dioxabicyclo[14.1.0]heptadecane-3-carboxamide;

[4S-[4R*,7S*,8R*,9R*,15R*]]-N-phenyl-4,8-dihydroxy-5,5,7,9,13-pentamethyl-2,6-dioxo-1-oxa-13-cyclohexadecene-16-carboxamide;

[4S-[4R*,7S*,8R*,9R*,15R*]]-N-phenyl-4,8-dihydroxy-5,5,7,9-tetramethyl-2,6-dioxo-1-oxa-13-cyclohexadecene-16-carboxamide;

[1S[1R*,3R*(E),7R*,10S*,11R*,12R*,16S*]]-7,11-dihydroxy-8,8,10,12,16-pentamethyl-3-[1-methyl-2-(2-methyl-4-thiazolyl)cyclopropyl]-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)cyclopropyl]-4,17-dioxabicyclo[14.1.0]heptadecane-5,9-dione;

[4S-[4R*,7S*,8R*,9R*,15R*(E)]]-4,8-dihydroxy-5,5,7,9,13-pentamethyl-16-[1-methyl-2-(2-hydroxymethyl-4-thiazolyl)ethenyl]-1-aza-13(Z)-cyclohexadecene-2,6-dione; and pharmaceutically acceptable salts, solvates and hydrates thereof.

Preferred compounds of Formula III for use in the methods of the invention include:

[1S-[1R*,3R*(E),7R*,10S*,11R*,12R*,16S*]]-3-[2-[2-(azidomethyl)-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-[[[(1,1-dimethylethoxy)carbonyl]amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[4S-[4R*,7S*,8R*,9R*,15R*(E)]]-16-[2-[2-[[[(1,1-dimethylethoxy)carbonyl]amino]methyl]-4-thiazolyl]-1-methylethenyl]-4,8-dihydroxy-5,5,7,9,13-pentamethyl-1-oxa-13(Z)-cyclohexadecene-2,6-dione;

[4S-[4R*,7S*,8R*,9R*,15R*(E)]]-16-[2-[2-(aminomethyl)-4-thiazolyl]-1-methylethenyl]-4,8-dihydroxy-5,5,7,9,13-pentamethyl-1-oxa-13(Z)-cyclohexadecene-2,6-dione;

[1S-[1R*,3R*(E),7R*,10S*,11R*,12R*,16S*]]-7,11-dihydroxy-8,8,10,12-tetramethyl-3-[1-methyl-2-[2-[(pentanoyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[(naphthoyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-dihydroxy-3-[2-[2-[[(2-methoxyethoxy)acetyloxy]methyl]-1-methyl-4-thiazolyl]ethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[(N-propionylamino)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-(3-acetyl-2,3-dihydro-2-methylene-4-thiazolyl)-1-methylethenyl]-7,11-dihydroxy-8,8,10,12-tetramethyl-4,17-dioxabicyclo[14.1.0]heptadecane-5,9-dione,N-oxide;

[1S-[1R*,3R*(E),7R*,10S*,11R*,12R*,16S*]]-7,11-dihydroxy-3-[2-[2-(methoxymethyl)-4-thiazolyl]-1-methylethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12,16-pentamethyl-3-[1-methyl-2-[2-(phenoxymethyl)-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-[2-[(ethylthio)methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-(ethoxymethyl)-4-thiazolyl]-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[(2,3,4,6-tetraacetyl-alpha-glucosyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[(2',3',4',6'-tetraacetyl-beta-glucosyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[(6'-acetyl-alpha-glucosyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-7,11-dihydroxy-8,8,10,12,16-pentamethyl-3-[1-methyl-2-[2-[(p-toluenesulfonyloxy)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-[2-(bromomethyl)-4-thiazolyl]-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-(5-bromo-2-methyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-[2-(cyanomethyl)-4-thiazolyl]-1-methylethenyl]-7,11-dihydroxy-8,8,10,12,16-pentamethyl-4,17-dioxabicyclo[14.1.0]heptadecane-5,9-dione;

[4S-[4R*,7S*,8R*,9R*,15R*(E)]]-16-[2-[2-(cyanomethyl)-4-thiazolyl]-1-methylethenyl]-4,8-dihydroxy-5,5,7,9,13-pentamethyl-1-oxa-13 (Z)-cyclohexadecene-2,6-dione;

[1S-[1R*,3R*(E),7R*,10S*,11R*,12R*,16S*]]-7,11-dihydroxy-3-[2-[2-(1H-imidazol-1-ylmethyl)-4-thiazolyl]-1-methylethenyl]-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-(2-formyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-(2-formyl-4-thiazolyl)-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-(2-ethenyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-3-[2-[2-(methoxyimino)-4-thiazolyl]-1-methylethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-[2-[[(phenylmethyl)imino]methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-(2-acetyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-(2-oxiranyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-dihydroxy-3-[2-[2-(2-iodoethenyl)-4-thiazolyl]-1-methylethenyl]-8,8,10,12-tetramethyl-4,17-dioxabicyclo[14.1.0]heptadecane-5,9-dione;

[1S-[1R*,3R*(E),7R*,10S*,11R*,12R*,16S*]]-3-[2-(2-ethynyl-4-thiazolyl)-1-methylethenyl]-7,11-dihydroxy-8,8,10,12-tetramethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12,16-pentamethyl-3-[1-methyl-2-[2-[(methylamino)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-3-[2-[2-[[[2-(dimethylamino)ethyl]amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-[(dimethylamino)methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-3-[2-[2-[[bis(2-methoxyethyl)amino]methyl]-4-thiazolyl]-1-methylethenyl]-7,11-dihydroxy-8,8,10,12,16-pentamethyl-4,17-dioxabicyclo[14.1.0]heptadecane-5,9-dione;

[1S-[1R*,3R*(E),7R*,10S*,11R*,12R*,16S*]]-7,11-dihydroxy-8,8,10,12,16-pentamethyl-3-[1-methyl-2-[2-[(4-methyl-1-piperazinyl)methyl]-4-thiazolyl]ethenyl]-4,17-dioxabicyclo[14.1.0]heptadecane-5,9-dione;

[1S-[1R*,3R*(E),7R*,10S*,11R*,12R*,16S*]]-4-[2-(7,11-dihydroxy-8,8,10,12-tetramethyl-5,9-dioxo-4,17-dioxabicyclo[14.1.0]heptadecan-3-yl)-1-propenyl]-2-thiazolecarboxylicacid;

[1S-[1R*,3R*(E),7R*,10S*,11R*,12R*,16S*]]-4-[2-(7,11-dihydroxy-8,8,10,12-tetramethyl-5,9-dioxo-4,17-dioxabicyclo[14.1.0]heptadecan-3-yl)-1-propenyl]-2-thiazolecarboxylic acid methyl ester; and the pharmaceutically acceptable salts, solvents and hydrates thereof.

The Formula II compounds may be prepared by the procedures described in WO 99/02514. The Formula III compounds may be prepared by the procedures described in U.S. Pat. No. 6,262,094.

The compounds of Formulas I, II, III, IIIa, and/or IV or analogs thereof are useful in various pharmaceutically acceptable salt forms. The term "pharmaceutically acceptable salt" refers to those salt forms which would be apparent to the pharmaceutical chemist, i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients or their pharmaceutically acceptable salts in combination with pharmaceutically acceptable carriers.

Pharmaceutically acceptable salts of the Formula I, II, IIIa, and/or IV or analogs thereof compounds which are suitable for use in the methods and compositions of the present invention include, but are not limited to, salts formed with a variety of organic and inorganic acids such as hydrogen chloride, hydroxymethane sulfonic acid, hydrogen bromide, methanesulfonic acid, sulfuric acid, acetic acid, trifluoroacetic acid, maleic acid, benzenesulfonic acid, toluenesulfonic acid, sulfamic acid, glycolic acid, stearic acid, lactic acid, malic acid, pamoic acid, sulfanilic acid, 2-acetoxybenzoic acid, fumaric acid, toluenesulfonic acid, methanesulfonic acid, ethanedisulfonic acid, oxalic acid, isethonic acid, and include various other pharmaceutically acceptable salts, such as, e.g., nitrates, phosphates, borates, tartrates, citrates, succinates, benzoates, ascorbates, salicylates, and the like. Cations such as quaternary ammonium ions are contemplated as pharmaceutically acceptable counterions for anionic moieties.

Preferred salts of Formula I, II, III, IIIa, and/or IV or analogs thereof compounds include hydrochloride salts, methanesulfonic acid salts and trifluoroacetic acid salts. In addition, pharmaceutically acceptable salts of the Formula I, II, III, IIIa, and/or IV or analogs thereof compounds may be formed with alkali metals such as sodium, potassium and lithium; alkaline earth metals such as calcium and magnesium; organic bases such as dicyclohexylamine, tributylamine, and pyridine; and amino acids such as arginine, lysine and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

As is known in the art, Ipilimumab refers to an anti-CTLA-4 antibody, and is a fully human IgG$_{1\kappa}$ antibody derived from transgenic mice having human genes encoding heavy and light chains to generate a functional human repertoire. Ipilimumab can also be referred to by its CAS Registry No. 477202-00-9, and is disclosed as antibody 10DI in PCT Publication No. WO01/14424, incorporated herein by reference in its entirety and for all purposes. Specifically, Ipilimumab describes a human monoclonal antibody or antigen-binding portion thereof that specifically binds to CTLA4, comprising a light chain variable region and a heavy chain variable region having a light chain variable region comprised of SEQ ID NO:5, and comprising a heavy chain region comprised of SEQ ID NO:6. Pharmaceutical compositions of Ipilimumab include all pharmaceutically acceptable compositions comprising Ipilimumab and one or more diluents, vehicles and/or excipients. Examples of a pharmaceutical composition comprising Ipilimumab are provided in PCT Publication No. WO2007/67959. Impilimumab may be administered by I.V.

Light Chain Variable Region for Impilimumab (SEQ ID NO: 1)
EIVLTQSPGTLSLSPGERATLSCRASQSVGSSYLAWYQQKPGQAPRLLIY

GAFSRATGIPDRFSGSGSGTDFTLTISRLEPEDFAVYYCQQYGSSPWTFG

QGTKVEIK

Heavy Chain Variable Region for Impilimumab (SEQ ID NO: 2)
QVQLVESGGGVVQPGRSLRLSCAASGFTFSSYTMHWVRQAPGKGLEWVTF

ISYDGNNKYYADSVKGRFTISRDNSKNTLYLQMNSLRAEDTAIYYCARTG

WLGPFDYWGQGTLVTVSS

As noted elsewhere herein, the administration of one or more anti-CTLA4 antagonists may be administered either alone or in combination with a peptide antigen (e.g., gp100), in addition to an anti-proliferative agent disclosed herein. A non-limiting example of a peptide antigen would be a gp100 peptide comprising, or alternatively consisting of, the sequence selected from the group consisting of: IMDQVPFSV (SEQ ID NO:3), and YLEPGPVTV (SEQ ID NO:4). Such a peptide may be administered orally, or preferably by injection s.c. at 1 mg emulsified in incomplete Freund's adjuvant (IFA) injected s.c. in one extremity, and 1 mg of either the same or a different peptide emulsified in IFA may be injected in another extremity.

The present invention also encompasses a pharmaceutical composition useful in the treatment of cancer, comprising the administration of a therapeutically effective amount of the combinations of this invention, with or without pharmaceutically acceptable carriers or diluents. The synergistic pharmaceutical compositions of this invention comprise an anti-proliferative agent or agents, a formula I compound, and a pharmaceutically acceptable carrier. The methods entail the use of a neoplastic agent in combination with a Formula I, II, III, IIIa, and/or IV or analogs thereof compound. The compositions of the present invention may further comprise one or more pharmaceutically acceptable additional ingredient(s) such as alum, stabilizers, antimicrobial agents, buffers, coloring agents, flavoring agents, adjuvants, and the like. The antineoplastic agents, Formula I, II, III, IIIa, and/or IV or analogs thereof compounds and compositions of the present invention may be administered orally or parenterally including the intravenous, intramuscular, intraperitoneal, subcutaneous, rectal and topical routes of administration.

For oral use, the antineoplastic agents, Formula I, II, III, IIIa, and/or IV or analogs thereof compounds and compositions of this invention may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc, and sugar. When aqueous suspensions are used for oral administration, emulsifying and/or suspending agents are commonly added.

In addition, sweetening and/or flavoring agents may be added to the oral compositions. For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled in order to render the preparation isotonic.

For preparing suppositories according to the invention, a low melting wax such as a mixture of fatty acid glycerides or cocoa butter is first melted, and the active ingredient is dispersed homogeneously in the wax, for example by stirring.

The molten homogeneous mixture is then poured into conveniently sized molds and allowed to cool and thereby solidify.

Liquid preparations include solutions, suspensions and emulsions. Such preparations are exemplified by water or water/propylene glycol solutions for parenteral injection. Liquid preparations may also include solutions for intranasal administration.

Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

The compounds of Formula I, II, III, IIIa, and/or IV or analogs thereof, as well as the anti-CTLA4 agents, described herein may also be delivered transdermally. The transdermal compositions can take the form of creams, lotions, aerosols and/or emulsions and can be included in a transdermal patch of the matrix or reservoir type as are conventional in the art for this purpose.

The combinations of the present invention may also be used in conjunction with other well known therapies that are selected for their particular usefulness against the condition that is being treated.

If formulated as a fixed dose, the active ingredients of the combination compositions of this invention are employed within the dosage ranges described below. Alternatively, the anti-CTLA4 agent, and I, II, III, IIIa and/or IV or analogs thereof compounds may be administered separately in the dosage ranges described below. In a preferred embodiment of the present invention, the anti-CTLA4 agent is administered in the dosage range described below following or simultaneously with administration of the Formula I, II, III, IIIa, and/or IV or analogs thereof compound in the dosage range described below.

The following sets forth preferred therapeutic combinations and exemplary dosages for use in the methods of the present invention. Where "Compound of Formula II" appears, any of the variations of Formula II or Formula III set forth herein are contemplated for use in the chemotherapeutic combinations. Preferably, Compound 1 or Compound 4 is employed.

| THERAPEUTIC COMBINATION | DOSAGE mg/m$^2$ (per dose) |
|---|---|
| Compound of Formula I (Ixabepilone) + | 1-500 mg/m$^2$ |
| anti-CTLA4 Antibody | 0.1-25 mg/kg |
| Compound of Formula II + | 0.1-100 mg/m$^2$ |
| anti-CTLA4 Antibody | 0.1-25 mg/kg |
| Compound of Formula III + | 0.1-100 mg/m$^2$ |
| anti-CTLA4 Antibody | 0.1-25 mg/kg |
| Compound of Formula IV (Paclitaxel) + | 40-250 mg/m$^2$ |
| anti-CTLA4 Antibody | 0.1-25 mg/kg |

While this table provides exemplary dosage ranges of the Formula I, Formula II, Formula III, IIIa and Formula IV compounds and certain anticancer agents of the invention, when formulating the pharmaceutical compositions of the invention the clinician may utilize preferred dosages as warranted by the condition of the patient being treated. For example, the compound of Formula I may preferably be administered at about 40 mg/m$^2$ every 3 weeks. Compound 1 may preferably be administered at about 25-60 mg/m$^2$ every 3 weeks. Compound 2, may preferably be administered at a dosage ranging from about 25-500 mg/m$^2$ every three weeks for as long as treatment is required. The compound of Formula IV may preferably be administered at about 135-175 mg/m$^2$ every three weeks.

The anti-CTLA4 antibody may preferably be administered at about 0.3-10 mg/kg, or the maximum tolerated dose. In an embodiment of the invention, a dosage of CTLA-4 antibody is administered about every three weeks. Alternatively, the CTLA-4 antibody may be administered by an escalating dosage regimen including administering a first dosage of CTLA-4 antibody at about 3 mg/kg, a second dosage of CTLA-4 antibody at about 5 mg/kg, and a third dosage of CTLA-4 antibody at about 9 mg/kg.

In another specific embodiment, the escalating dosage regimen includes administering a first dosage of CTLA-4 antibody at about 5 mg/kg and a second dosage of CTLA-4 antibody at about 9 mg/kg.

Further, the present invention provides an escalating dosage regimen, which includes administering an increasing dosage of CTLA-4 antibody about every six weeks.

In an aspect of the present invention, a stepwise escalating dosage regimen is provided, which includes administering a first CTLA-4 antibody dosage of about 3 mg/kg, a second CTLA-4 antibody dosage of about 3 mg/kg, a third CTLA-4 antibody dosage of about 5 mg/kg, a fourth CTLA-4 antibody dosage of about 5 mg/kg, and a fifth CTLA-4 antibody dosage of about 9 mg/kg. In another aspect of the present invention, a stepwise escalating dosage regimen is provided, which includes a first dosage of 5 mg/kg, a second dosage of 5 mg/kg, and a third dosage of 9 mg/kg.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

Certain cancers can be treated effectively with compounds of Formula I, II, III, IIIa, and/or IV and a one or more anti-CTLA4 agents. Such triple and quadruple combinations can provide greater efficacy. When used in such triple and quadruple combinations the dosages set forth above can be utilized.

When employing the methods or compositions of the present invention, other agents used in the modulation of tumor growth or metastasis in a clinical setting, such as antiemetics, can also be administered as desired.

The present invention encompasses a method for the synergistic treatment of cancer wherein anti-CTLA4 agent and a Formula I, II, III, IIIa, and/or IV compound are administered simultaneously or sequentially. Thus, while a pharmaceutical formulation comprising anti-CTLA4 agent(s) and a Formula I, II, III, IIIa, and/or IV compound may be advantageous for administering the combination for one particular treatment, prior administration of the anti-CTLA4 agent(s) may be advantageous in another treatment. It is also understood that the instant combination of anti-CTLA4 agent(s) and Formula I, II, III, IIIa, and/or IV compound may be used in conjunction with other methods of treating cancer (preferably cancerous tumors) including, but not limited to, radiation therapy and surgery. It is further understood that a cytostatic or quiescent agent, if any, may be administered sequentially or simultaneously with any or all of the other synergistic therapies.

The combinations of the instant invention may also be co-administered with other well known therapeutic agents that are selected for their particular usefulness against the condition that is being treated. Combinations of the instant invention may alternatively be used sequentially with known pharmaceutically acceptable agent(s) when a multiple combination formulation is inappropriate.

The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., anti-CTLA4 agent(s)) on the patient, and in view of the observed responses of the disease to the administered therapeutic agents.

In the methods of this invention, a compound of Formula I, II, III, IIIa or Formula IV is administered simultaneously or sequentially with an anti-CTLA4 agent. Thus, it is not necessary that the anti-CTLA4 therapeutic agent(s) and compound of Formula I, II, III, IIIa, and/or IV, be administered simultaneously or essentially simultaneously. The advantage of a simultaneous or essentially simultaneous administration is well within the determination of the skilled clinician.

Also, in general, the compound of Formula I, II, III, IIIa, and/or IV, and anti-CTLA4 agent(s) do not have to be administered in the same pharmaceutical composition, and may, because of different physical and chemical characteristics, have to be administered by different routes. For example, the compound of Formula I, II, III, IIIa or IV may be administered intravenously to generate and maintain good blood levels thereof, while the anti-CTLA4 agent(s) may also be administered intravenously. Alternatively, the compound of Formula I, II, III, IIIa or IV may be administered orally to generate and maintain good blood levels thereof, while the anti-CTLA4 agent(s) may also be administered intravenously. Alternatively, the compound of Formula I, II, III, IIIa or IV may be administered intravenously to generate and maintain good blood levels thereof, while the anti-CTLA4 agent(s) may also be administered orally. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of compound of Formula I, II, III, IIIa, and/or IV or analogs thereof and anti-CTLA4 agent(s) will depend upon the diagnosis of the attending physicians and their judgment of the condition of the patient and the appropriate treatment protocol.

If the compound of Formula I, II, III, IIIa, and/or Formula IV and the anti-CTLA4 agent(s) are not administered simultaneously or essentially simultaneously, then the initial order of administration of the compound of Formula I, II, III, IIIa, and/or IV, and the anti-CTLA4 agent(s) may be varied. Thus, for example, the compound of Formula I, II, III, IIIa, and/or IV or analogs thereof may be administered first followed by the administration of the anti-CTLA4 agent(s); or the anti-CTLA4 agent(s) may be administered first followed by the administration of the compound of Formula I, II, III, IIIa, and/or IV. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the anti-CTLA4 agent(s) may be administered initially. The treatment is then continued with the administration of the compound of Formula I, II, III, IIIa, and/or IV or analogs thereof and optionally followed by administration of a cytostatic agent, if desired, until the treatment protocol is complete. Alternatively, the administration of the compound of Formula I, II, III, IIIa, and/or IV or analogs thereof and optionally followed by administration of a cytostatic agent may be administered initially. The treatment is then continued with the administration of the anti-CTLA4 agent(s), until the treatment protocol is complete.

Thus, in accordance with experience and knowledge, the practicing physician can modify each protocol for the administration of a component (therapeutic agent—i.e., compound of Formula I, II, III, IIIa, and/or IV or analogs thereof, anti-CTLA4 agent(s)) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

In order to facilitate a further understanding of the invention, the following examples are presented primarily for the purpose of illustrating more specific details thereof. The scope of the invention should not be deemed limited by the examples, but to encompass the entire subject matter defined by the claims.

REFERENCES

1. Long, B. H. et al., "Mechanisms of resistance to etoposide and teniposide in acquired resistant human colon and lung carcinoma cell lines", *Cancer Res.*, 51:5275-5284 (1991).
2. Giannakakou, P. et al., "Paclitaxel-resistant human ovarian cancer cells have mutant beta-tubulins that exhibit impaired paclitaxel-driven polymerization", *J. Biol. Chem.*, 272(27):17118-17125 (1997).
3. Riss, T. L. et al., "Comparison of MTT, XTT, and a novel tetrazolium compound MTS for in vitro proliferation and chemosensitivity assays", *Mol. Biol. Cell,* 3 (Suppl.):184a (1992).
4. Stephens, T. C. et al., "The evaluation of combinations of cytotoxic drugs and radiation: Isobolograms and therapeutic synergism", *Rodent Tumor Models in Experimental Cancer Therapy*, p. 248. Pergamon Press, NY, publ., Kallman, R. F., ed.
5. Long, B. H., "Paclitaxel inhibits progression of mitotic cells to G(1) phase by interference with spindle formation without affecting other microtubule functions during anaphase and telophase", *Cancer Res.,* 54(16):4355-4361 (1994).

6. Williams, R. C. et al., "Preparation of tubulin from brain", *Meth. Enzymol.*, 85(Pt. D):376-385 (1982).
7. Gehan, G. A., "A generalized Wilcoxon test for comparing arbitrarily singly-censored samples", *Biometrika*, 52:203-233 (1985).
8. Walunas, T. L. et al., "CTLA-4 can function as a negative regulator of T cell activation", *Immunity*, 1(5):405-413 (August 1994).
9. Bretscher, P. et al., *Science*, 169:1042-1049 (1970).
10. Schwartz, R. H., *Science*, 248:1349-1356 (1990).
11. Linsley, P. S. et al., *J. Exp. Med.*, 173:721-730 (1991).
12. Linsley, P. S. et al., *J. Exp. Med.*, 174:561-569 (1991).
13. Brunet, J. F. et al., *Nature*, 328:267-270 (1987).
14. Gross, J. A. et al., *J. Immunol.*, 149:380-388 (1992).
15. Alegre, M. L. et al., *Nat. Rev. Immunol.*, 1:220-228 (2002).
16. Lindsten, T. et al., *J. Immunol.*, 151:3489-3499 (1993).
17. Walunas, T. L. et al., *Immunity*, 1:405-413 (1994).
18. Linsley, P. S. et al., *Immunity*, 1:793-801 (1994).
19. Walunas, T. L. et al., *J. Exp. Med.*, 183:2541-2550 (1996).
20. Krummel, M. F. et al., *J. Exp. Med.*, 183:2533-2540 (1996).
21. Brunner, M. C. et al., *J. Immunol.*, 162:5813-5820 (1999).
22. Greenwald, R. J. et al., *Eur. J. Immunol.*, 32:366-373 (2002).
23. Leach, D. R. et al., *Science*, 271:1734-1736 (1996).
24. van Elsas, A. et al., *J. Exp. Med.*, 190:355-366 (1999).
25. van Elsas, A. et al., *J. Exp. Med.*, 194:481-489 (2001).
26. Hurwitz, A. A. et al., *Cancer Res.*, 60:2444-2448 (2000).

EXAMPLE 1

Method of Assessing the Effect of the Combination of Microtubulin Stabilizing Agents with Anti-CTLA4 Blockade on Tumor Growth in a SA1N Fibrosarcoma Tumor Model in Vitro Background The antitumor activity of a homolog of ipilimumab, a CTLA-4 blocking agent, was investigated in combination with ixabepilone, a microtubule-stabilizing drug, in preclinical studies. The inventors hypothesized that this combinatorial approach may produce therapeutic synergy based on their unique mechanism of action and cellular targets.

Ixabepilone induces tumor cell necrosis thus providing a source of tumor antigens and changes in tumor architecture that facilitate T-cell priming and infiltration, whereas CTLA-4 blocking mAb promotes expansion and infiltration of tumor-primed cytolytic T cells.

Methods

Efficacy studies were conducted in 3 different tumor lines implanted in immunocompetent mice: SA1N fibrosarcoma, MI09 lung carcinoma and EMT-6 mammary carcinoma. Ixabepilone and CTLA-4 mAb were administered at their optimal dose and schedule: ixabepilone, 8 mglkg; CTLA-4 mAb, 20 mglkg every 4 days for 3 doses. For the combination group, anti-CTLA-4 mAb was administered one day after each ixabepilone treatment. In selected studies, animals with complete tumor regressions were rechallenged with a lethal dose of tumor cells to determine the level of immune protection. In other studies, the combined efficacy of CTLA-4 mAb+ixabepilone was compared directly with CTLA-4 lnAb+paclitaxel.

Results

The combination of the ipilimumab homolog CTLA-4 mAb and ixabepilone showed a synergistic anti-tumor effect in all tumor models tested causing long-lasting complete responses in 70-100% of the animals, demonstrating superior efficacy compared to each treatment alone (p<0.05). Furthermore, animals treated with ixabepilone and CTLA-4 mAb rejected a subsequent tumor rechallenge suggesting the development of a protective memory immune response. Conversely, ixabepilone-treated animals showed only partial protection, as evident by a delay in tumor growth compared to naive mice. Combination treatments were well-tolerated with no evidence for increased toxicity. The CTLA-4 mAb+ixabepilone combination yielded superior efficacy than CTLA-4+paclitaxel.

Conclusions

These findings provide evidence that the combination of ixabepilone and ipilimumab homolog CTLA-4 blocking mAb elicits effective and long-lasting anti-tumor effects and warrant investigation of ipilimumab and ixabepilone regimen in clinical trials.

EXAMPLE 2

Method of Assessing the Effect of the Combination of Microtubulin Stabilizing Agents with Anti-CTLA4 Blockade on Tumor Growth in a SA1N Fibrosarcoma Tumor Model In Vivo Chemoimmunotherapy is a novel approach for cancer treatment which consists of the combination of chemotherapeutic and immunotherapeutic agents. This approach combines the effects of chemotherapy which elicits a direct attack on tumor cells resulting in tumor cell necrosis or apoptosis, and, agents that modulate host immune responses to tumor antigens. The effect of an anti-mouse CTLA-4 blocking antibody, the murine homolog of ipilimumab, was evaluated in multiple murine tumor models in combination with the microtubule-stabilizing agents paclitaxel (TAXOL®), and ixabepilone (IXEMPRA™). Efficacy studies were conducted in 5 different tumor lines: SA1N fibrosarcoma, M109 lung carcinoma, EMT-6 mammary carcinoma, CT-26 colon carcinoma and B16 melanoma. Ixabepilone, paclitaxel and CTLA-4 mAb were administered at their optimal dose and schedule: ixabepilone, 8 mg/kg; paclitaxel, 24 mg/kg, CTLA-4 mAb, 20 mg/kg every 4 days for 3 doses. For the combination group, anti-CTLA-4 mAb was administered one day after each ixabepilone or paclitaxel treatment. In selected studies, animals with complete tumor regressions were rechallenged with a lethal dose of tumor cells to determine the level of immune protection. The combination of the ipilimumab homolog CTLA-4 mAb and ixabepilone showed a synergistic anti-tumor effect in all tumor models tested except for the B16 melanoma, causing long-lasting complete responses in 70-100% of the animals, demonstrating superior efficacy compared to each treatment alone (p<0.05). Furthermore, animals treated with ixabepilone+CTLA-4 mAb rejected a subsequent tumor rechallenge suggesting the development of a protective memory immune response. Conversely, ixabepilone-treated animals showed only partial protection, as evident by a delay in tumor growth. Combination treatments were well-tolerated. Combination of paclitaxel and CTLA-4 blockade also showed synergy in 2 out of 5 models tested. These findings provide evidence that the combination of ixabepilone and ipilimumab homolog CTLA-4 blocking mAb elicits effective and long-lasting anti-tumor effects and warrant investigation of ipilimumab and ixabepilone regimen in clinical trials.

Materials and Methods

Antibodies

The hybridoma for the anti-CTLA-4 monoclonal antibody (mAb), clone 4F10-UC10 (Walunas et al., *Immunity*, 1(5): 405-413 (August 1994)), was obtained from the American Tissue Type Collection (Manassas, Va.). Antibody UC10 (hamster IgG anti-mouse CTLA-4) was produced and purified by BMS (Protein Therapeutics Division, Hopewell, N.J., USA). Anti-CTLA-4 was certified to have <0.5 EU/mg endotoxin levels, >95% purity and <5% high molecular weight species. Stock solutions of anti-CTLA-4 were kept at −80° C. and were thawed out at 4° C. prior to use. Control antibody consisted of a polyclonal hamster IgG (Jackson ImmunoResearch, West Grove, Pa.). Dosing solutions of Anti-CTLA-4 and hamster IgG control were prepared weekly in sterile phosphate buffered saline (pH 7.0).

Animals

Eight to twelve week-old female BALB/c, A/J or C57/BL6 mice were purchased from Harlan, Indianapolis, Ind. Mice received food and water ad libitum, and were maintained in a controlled environment according to AALAC regulations.

Tumor Models

Tumor cell lines were maintained in vitro. Treatments were initiated when the subcutaneous tumors reached a median size between 100-200 mm³ (established model) or prior to detection (initiation model). Tumors were measured twice weekly and tumor size (mm³) was calculated as (length× width)/2. Body weights were obtained weekly. The tumor models used in these studies are outlined in Table 1.

Efficacy Studies

The dose levels, routes and dosing schedules are indicated for each particular study described below. Antibodies and chemotherapeutic agents were administered intraperitoneally (i.p.). Each treatment regimen consisted of a cohort of eight to ten mice. Anti-tumor activity, defined as percentage tumor growth inhibition, was calculated as follows:

% Tumor Growth Inhibition=100−[(Tt/To)/(Ct/Co)]/ 100−(Ct/Co)

where,

Tt=median tumor size of treated group at the end of treatment

To=median tumor size of treated group at treatment initiation

Ct=median tumor size of control group at the end of treatment

Co=median tumor size at treatment initiation

In addition, another parameter used to define efficacy was to determine time to tumor progression to target size (T-C), where the time (days) for the median tumor size of control (C) mice to reach target size was subtracted to the time for median tumor size of treated (T) mice to reach target size. A delay in reaching target size by the treated groups of >than one tumor volume doubling time (TVDT) was considered an active result.

Statistical Analysis

Nonparametric analysis using the Wilcoxon test was used to determine statistical significance.

Results

SA1N fibrosarcoma is an inherently immunogenic tumor line which is sensitive to the effects of CTLA-4 blockade. Two studies were conducted to determine the effect of CTLA-4 blockade in combination with ixabepilone or paclitaxel in this tumor model (see Table 1). Animals were implanted with SA1N cells subcutaneously and treatments were initiated when tumors reached 100-150 mm³. Experimental groups consisted of cohorts of 8 mice. Ixabepilone, paclitaxel and CTLA-4 mab were administered intraperitoneally (IP) every 4 days for 3 doses. In the combination groups, CTLA-4 mab was administered one day after each chemotherapy treatment.

CTLA-4 mAb was effective producing % tumor growth inhibition (TGI) values of 65-90%, with delay in tumor growth and 25-50% complete regressions (CR, see Table 2). Ixabepilone was also effective in this model producing % TGI of 92 and 83, with 3 out of 8 mice showing complete regressions in one study. Moreover, when CTLA-4 mAb was tested in combination with ixabepilone, synergistic effects were observed in both studies with a high number of complete regressions (71.4; 87.5% CR, see Table 2).

Similarly, the effect of CTLA-4 mAb in combination with paclitaxel was studied in 2 independent studies (Table 2). Paclitaxel showed a variable effect in these studies, whereas CTLA-4 mab showed similar antitumor effects in both. Nevertheless, in both studies combination of CTLA-4 mAb with paclitaxel resulted in synergistic effects with long lasting complete responses (see Table 2).

TABLE 1

Characteristics of the Tumor Lines used in Efficacy Studies (MFR$^a$)

| Tumor Line | Mouse Strain | Origin | MHC Class I | CD137L | CD137 | B7.1 | B7.2 |
|---|---|---|---|---|---|---|---|
| SA1N | A/J | Fibrosarcoma | | | | | |
| EMT-6 | Balb/c | Mammary Ca | 5 | 1 | 1 | 35 | 10 |
| M109 | Balb/c | Lung Ca | 2.7 | 14 | 1 | 2 | 1 |
| CT-26 | Balb/c | Colon | | | | | |
| B16-F10-Luc | C57/BL6 | Melanoma | | | | | |

TABLE 2

Antitumor Activity of CTLA-4 Blockade in Combination with Various
Microtubule-stabilizing Agents in the SA1N Fibrosarcoma Tumor Model

| Study # | Treatment | Dose (mg/kg) | Schedule | Route | % TGI[a] | T – C (days)[b] | CR/Total # mice | Best Combination Effect |
|---|---|---|---|---|---|---|---|---|
| 9 | CTLA-4 mAb[c] | 20 | Day 11, 15, 19 | IP | 90 | 11 | 4/8 (50) | |
|  | Ixabepilone | 8 | Day 10, 14, 18 | IP | 92 | 11 | 3/8 (37.5) | |
|  | Ixabepilone | 8 | Day 10, 14, 18 | IP | 110 | >39 | 7/8 (87.5) | Therapeutic |
|  | CTLA-4 mAb | 20 | Day 11, 15, 19 | IP | | | | synergy[d] |
| 17 | CTLA-4 mAb[c] | 20 | Day 12, 16, 20 | IP | 79 | 7 | 2/8 (25) | |
|  | Ixabepilone | 8 | Day 11, 15, 19 | IP | 83 | 7 | 0/8 (0) | |
|  | Ixabepilone | 8 | Day 11, 15, 19 | IP | 112 | >95 | 5/7 (71) | Therapeutic |
|  | CTLA-4 mAb | 20 | Day 12, 16, 20 | IP | | | | synergy[d] |
| 11 | CTLA-4 mAb | 20 | Day 11, 15, 19 | IP | 65 | 6 | 2/8 | |
|  | Paclitaxel | 24 | Day 10, 14, 18 | IP | 88 | 13 | 3/8 | |
|  | Paclitaxel | 24 | Day 10, 14, 18 | IP | 122 | >28 | 7/8 | Therapeutic |
|  | CTLA-4 mAb | 20 | Day 11, 15, 19 | IP | | | | synergy[e] |
| 17 | CTLA-4 mAb | 20 | Day 11, 15, 19 | IP | 79 | 7 | 2/8 | |
|  | Paclitaxel | 24 | Day 10, 14, 18 | IP | 0 | 0 | 0/8 | |
|  | Paclitaxel | 24 | Day 10, 14, 18 | IP | 112 | >95 | 7/8 | Therapeutic |
|  | CTLA-4 mAb | 20 | Day 11, 15, 19 | IP | | | | synergy[e] |

[a] % TGI = % Tumor Growth Inhibition calculated on the last measurement for control group. Study 9 = Day 36; Study 11 = Day 34; Study 17 = Day 33
[b] T – C = Number of days for treated group to reach target size – number of days for control group to reach target size. Target size = 500 mm$^3$. Studies were terminated on the following days: day 39 for Study #9, day 52 for Study #11 and day 116 for Study #17
[c] In Studies #9 and #17 one CR, non-treatment related, was observed in the control group
[d] Combination treatment produced a significant enhancement of the antitumor activity compared to CTLA-4 mAb or ixabepilone alone (p < 0.05)
[e] Combination treatment produced a significant enhancement of the antitumor activity compared to CTLA-4 mAb or paclitaxel alone (p < 0.05)

EXAMPLE 3

Method of Assessing the Effect of the Combination of Microtubulin Stabilizing Agents with Anti-CTLA4 Blockade on Tumor Growth in a EMT-6 Mammary Carcinoma Tumor Model In Vivo EMT-6 is a low immunogenic tumor line with modest sensitivity to CTLA-4 mAb blockade only when treatments are initiated before tumors are established. As shown in Table 3, CTLA-4 mAb and ixabepilone elicited an antitumor effect with a T-C of 29 and 19 respectively. Paclitaxel was ineffective. Combination of ixabepilone plus CTLA-4 mAb produced a synergistic effect with a T-C >37 days and 100% of mice free of tumors. In this tumor model, CTLA-4 mAb plus paclitaxel did not show any additional antitumor effect when compared with the effect elicited by CTLA-4 mAb alone.

TABLE 3

Antitumor Activity of CTLA-4 mAb in Combination with Ixabepilone
or Paclitaxel in the EMT-6 Mammary Tumor Model

| Study # | Treatment | Dose (mg/kg) | Schedule | Route | T – C (days) | % Tumor-free Mice | Effect |
|---|---|---|---|---|---|---|---|
| 27 | CTLA-4 mAb | 20 | Day 4, 8, 12 | IP | 29 | 40 | |
|  | Ixabepilone | 8 | Day 3, 7, 11 | IP | 19 | 20 | |
|  | CTLA-4 mAb | 20 | Day 4, 8, 12 | IP | >37 | 100 | Therapeutic |
|  | Ixabepilone | 8 | Day 3, 7, 11 | IP | | | synergy[a] |
|  | Paclitaxel | 24 | | | 0 | 0 | |
|  | CTLA-4 mAb | 20 | Day 4, 8, 12 | IP | 37 | 40 | None |
|  | Paclitaxel | 24 | Day 3, 7, 11 | IP | | | |

[a] Combination treatment produced a significant enhancement of the antitumor activity compared to CTLA-4 mAb or ixabepilone alone (p < 0.05)

Figure 3:
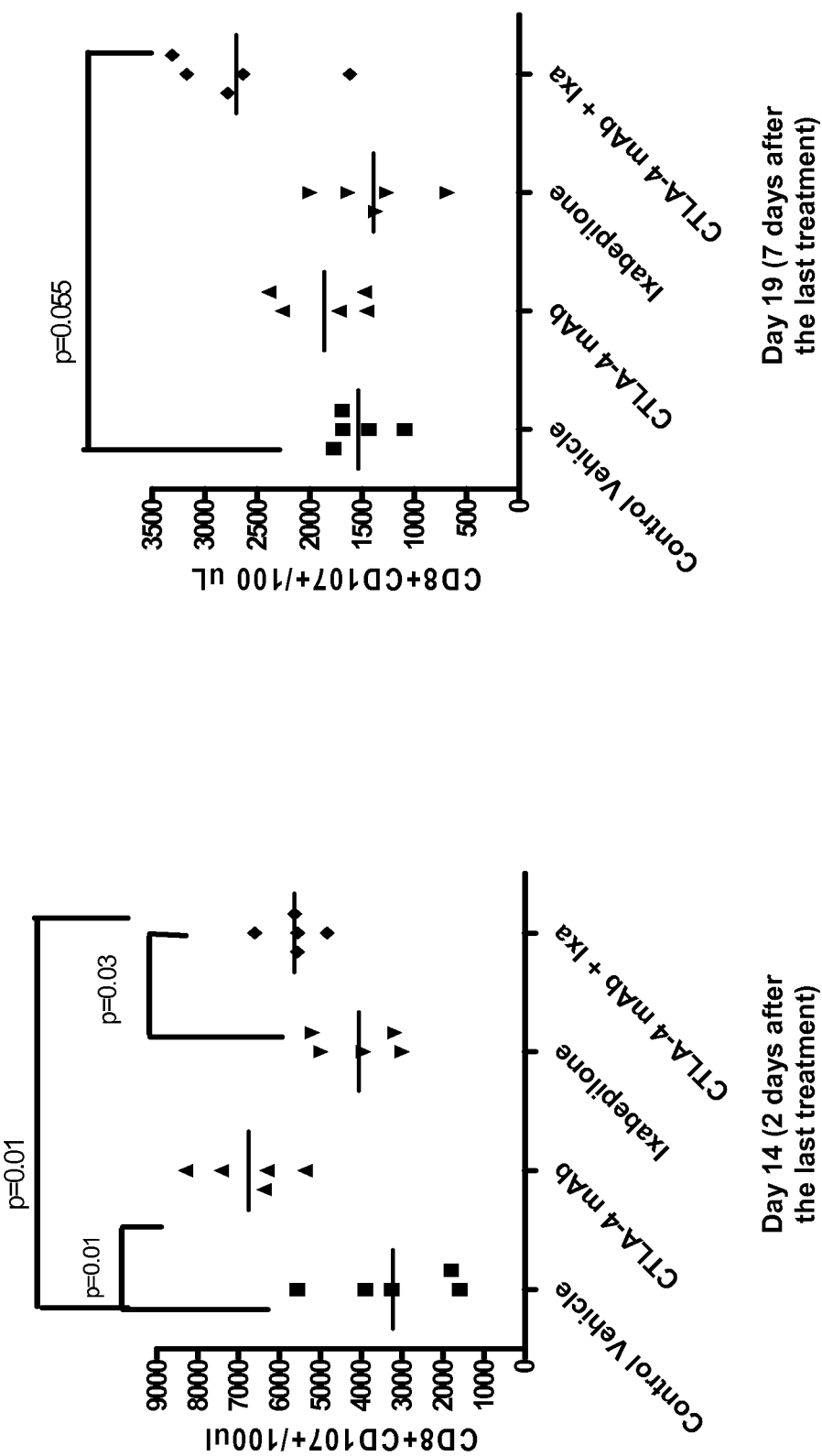
FIG. 3 shows treatment with CTLA-4 antibody and CTLA-4 antibody plus ixabepilone resulted in an increased number of $CD8^+CD107^+$ T cells 2 days after treatment, as well as a more persistent effect 7 days after treatment relative to either CTLA-4 antibody or ixabepilone alone.

In some studies, lymph nodes from mice under the same protocol were collected 2 and 7 days after the last treatment with CTLA-4 mAb. Lymph node cells were stained with monoclonal antibodies to CD4, CD8, and CD107 to determine the number of cytotoxic effector T cells. As shown in FIG. 3, treatment CTLA-4 antibody and CTLA-4 antibody plus ixabepilone increased the number of $CD8^+CD107^+$ T cells 2 days after treatment, and resulted in a more persistent effect 7 days after treatment relative to either CTLA-4 antibody or ixabepilone alone.

EXAMPLE 4

Method of Assessing the Effect of the Combination of Microtubulin Stabilizing Agents with Anti-CTLA4 Blockade on Tumor Growth in a M109 Lung Carcinoma Model In Vivo The antitumor effects of CTLA-4 mAb and microtubule-stabilizing agents were also studied in the M109 lung carcinoma model, a tumor line which is not sensitive to the effect of CTLA-4 blockade. In these studies treatments with chemotherapeutic agents were initiated when tumors were palpable, on day 3 after tumor implantation. This regimen was selected to produce a measurable antitumor effect, which was not observed when treatments were initiated at a later time. As in the studies conducted in the SA1N and EMT-6 tumor lines, CTLA-4 mAb was dosed one day after treatment with chemotherapy.

CTLA-4 mAb or paclitaxel treatments did not produce antitumor effects. On the other hand, ixabepilone was very effective inhibiting tumor growth in 50% of the treated animals. Combination of paclitaxel+CTLA-4 mAb produced a modest effect on tumor growth with an 80% of tumor incidence. Furthermore, combination of ixabepilone and CTLA-4 mAb produced a better effect than ixabepilone alone with 8 out of 10 mice free of tumor (20% tumor incidence, Table 2).

To determine whether the combination of CTLA-4+ixabepilone produced a memory immune response able to reject a secondary tumor challenge, animals free of tumors by day 97 were re-challenge with a lethal M109 cell inoculum. For this part of the study, M109 cells were injected into: a) 10 naïve mice (to control for tumor growth); and in study mice free of tumors: b) 5 mice previously treated with ixabepilone and c) 8 mice previously treated with ixabepilone+CTLA-4 mAb. All control mice developed progressive tumors with a median tumor size of 1000 mm$^3$ 10 days later whereas 4 out of 5 mice in the Ixabepilone-treated mice developed tumors (80%). The observation that one animal rejected M109 rechallenge suggests that ixabepilone alone may produce an effect in eliciting an antitumor immune response. Conversely, only 2 out of 8 mice in the ixabepilone+CTLA-4 mAb-treated group developed tumors (25%), suggesting that the addition of CTLA-4 mAb to ixabepilone elicited a memory immune response able to reject a secondary tumor challenge (Table 4, FIG. 1).

TABLE 4

Antitumor Activity of CTL-4 mAb in Combination with Microtubule-stabilizing Agents in the M109 Lung Carcinoma Tumor Model (M109 #40)

| Study # | Treatment | Dose (mg/kg) | Schedule | Route | % Tumor-Free Mice after Initial Tumor Implantation[a] | % Tumor-Free Mice following Rechallenge[b] |
|---|---|---|---|---|---|---|
| 40 | CTLA-4 mAb | 20 | Days 4, 8, 12 | IP | 100 | N/A |
| | Ixabepilone | 8 | Days 3, 7, 11 | IP | 50 | 75 |
| | Ixabepilone + CTLA-4 mAb | 24 | Days 3, 7, 11 Days 4, 8, 12 | IP | 20 | 25 |
| | Paclitaxel | 24 | Days 3, 7, 11 | IP | 100 | N/A |
| | Paclitaxel + CTLA-4 mAb | 24 | Days 3, 7, 11 Days 4, 8, 12 | IP | 80 | N/A |

[a]Percentage of animals that develop tumors following implantation on Day 0.
[b]Percentage of mice that develop tumors after tumor rechallenge on Day 95.

EXAMPLE 5

Figure 2:
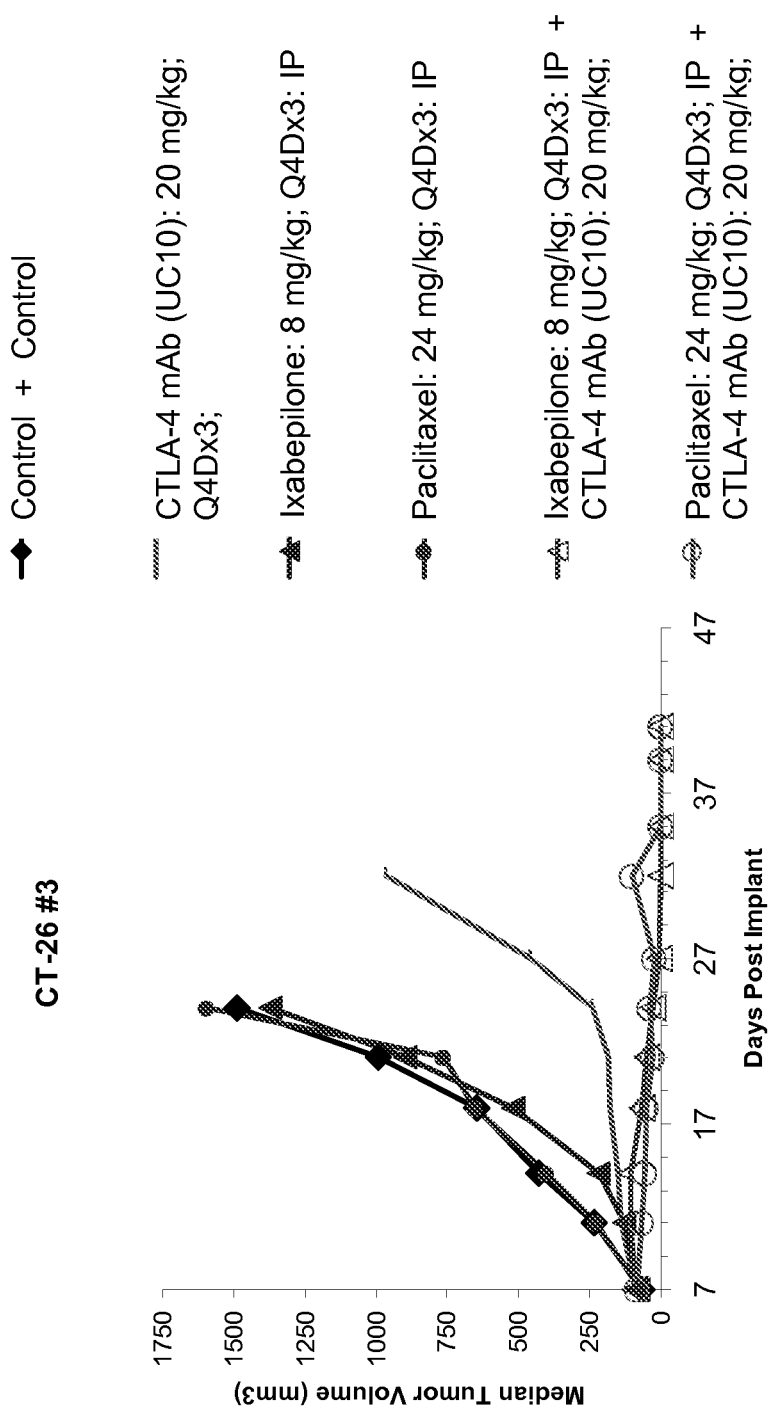
FIG. 2 shows the antitumor activity of CTLA-4 mAb in combination with paclitaxel and ixabepilone in a murine CT-26 colon tumor model. As shown, synergism was observed with both the combination of anti-CTLA-4 antibody and ixabepilone, as well as the combination of anti-CTLA-4 antibody and paclitaxel.

Method of Assessing the Effect of the Combination of Microtubulin Stabilizing Agents with Anti-CTLA4 Blockade on Tumor Growth in CT26 Colon Carcinoma In Vivo Next, the antitumor effects of CTLA-4 mAb and microtubule-stabilizing agents were studied in a model not sensitive to ixabepilone or paclitaxel, the CT26 colon carcinoma model. In this tumor line, CTLA-4 mAb treatment produced a modest antitumor effect as shown in Table 4 (2 out of 10 CRs). Even though neither paclitaxel or ixabepilone produced any measurable antitumor activity, combination of CTLA-4 mAb plus these agents produced long lasting tumor rejection in the majority of mice (Table 5, FIG. 2).

TABLE 5

Antitumor Activity of CTLA-4 mAb in Combination with Microtubule-stabilizing Agents in the CT26 Colon Tumor Model

| Treatment | Dose (mg/kg) | Schedule | Route | % Complete Regressions/ Total # mice |
|---|---|---|---|---|
| CTLA-4 mAb | 20 | Days 5, 9, 13 | IP | 2/10 |
| Ixabepilone | 8 | Days 4, 8, 12 | IP | 0/10 |
| Ixabepilone + CTLA-4 mAb | 24 | Days 4, 8, 12 Days 5, 9, 13 | IP | 7/10[a] |
| Paclitaxel | 24 | Days 4, 8, 12 | IP | 0/10 |
| Paclitaxel + CTLA-4 mAb | 24 | Days 4, 8, 12 Days 5, 9, 13 | IP | 5/10[b] |

[a]Combination treatment produced a significant enhancement of the antitumor activity compared to CTLA-4 mAb or ixabepilone alone (p < 0.05)
[b]Combination treatment produced a significant enhancement of the antitumor activity compared to CTLA-4 mAb or paclitaxel alone (p < 0.05)

In some studies, lymph nodes were collected 2 days after the last CTLA-4 mAb treatment and subjected to immunophenotyping. As shown in FIG. 4, treatment with CTLA-4 mAb increased the number of CD4 and CD8 activated T cells (CD4$^+$CD69$^+$; CD8$^+$CD69$^+$). Addition of ixabepilone or paclitaxel to CTLA-4 mAb treatment did not alter the expansion of activated T cells elicited by CTLA-4 mAb treatment.

Conclusion

In summary, synergistic effects were observed with the combination of CTLA-4 blocking mAb plus ixabepilone or paclitaxel in several tumor models which warrants the investigation of their combined effects in clinical trials. Ixabepilone+CTLA-4 mAb combination showed superior effects than paclitaxel+CTLA-4 mAb in the EMT-6 and M109 tumor models. Importantly, addition of CTLA-4 mAb to ixabepilone resulted in the generation of a memory immune response able to reject a secondary tumor challenge. Combination treatments expanded activated and cytolytic CD8 T cell population, supporting the synergistic efficacy seen in tumor growth inhibition (p<0.05). Additional studies are ongoing to understand the mechanisms underlying these synergistic effects.

The present invention is not limited to the embodiments specifically described above, but is capable of variation and modification without departure from the scope of the appended claims.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, GENBANK® Accession numbers, SWISS-PROT® Accession numbers, or other disclosures) in the Background of the Invention, Detailed Description, Brief Description of the Figures, and Examples is hereby incorporated herein by reference in their entirety. Further, the hard copy of the Sequence Listing submitted herewith, in addition to its corresponding Computer Readable Form, are incorporated herein by reference in their entireties.

---

What is claimed is:

1. A method for the treatment of cancer, comprising the administration to a mammal in need thereof a synergistic, therapeutically effective amount of (1) ipilimumab; and (2) ixabepilone, said cancer is selected from the group consisting of: lung cancer and breast cancer.

2. The method according to claim 1, wherein said treatment is administered intravenously.

3. The method according to claim 1, wherein ipilimumab is administered at a dose of about 3 mg/kg.

4. The method according to claim 1, wherein ixabepilone is administered at a dose of about 40 mg/m$^2$.

5. The method according to claim 1, wherein said treatment is administered about once every three weeks.

* * * * *

UNITED STATES PATENT AND TRADEMARK OFFICE
CERTIFICATE OF CORRECTION

| | | Page 1 of 1 |
|---|---|---|
| PATENT NO. | : 8,449,886 B2 | |
| APPLICATION NO. | : 12/811867 | |
| DATED | : May 28, 2013 | |
| INVENTOR(S) | : Maria Jure-Kunkel | |

It is certified that error appears in the above-identified patent and that said Letters Patent is hereby corrected as shown below:

OTHER PUBLICATIONS under item (56) – Title Page 2

Add the following reference:

Walunus, et al., "CTLA-4 Ligation Blocks CD28-dependent T Cell Activation", J. Exp. Med., vol. 183, pp. 2541-2550 (1996)

Signed and Sealed this
Third Day of September, 2013

Teresa Stanek Rea
*Acting Director of the United States Patent and Trademark Office*